(12) United States Patent
Kwon et al.

(10) Patent No.: US 10,338,061 B2
(45) Date of Patent: Jul. 2, 2019

(54) METHOD FOR DIAGNOSIS OF DISEASES USING MORPHOLOGICAL CHARACTERISTICS OF LUTERIAL

(71) Applicants: Young Ah Kwon, Seoul (KR); Won Cheol Choi, Gyeonggi-do (KR); Suk Hoon Choi, Seoul (KR); Chang Hoon Choi, Seoul (KR)

(72) Inventors: Young Ah Kwon, Seoul (KR); Won Cheol Choi, Gyeonggi-do (KR); Suk Hoon Choi, Seoul (KR); Chang Hoon Choi, Seoul (KR)

(73) Assignees: Young Ah Kwon, Seoul (KR); Won Cheol Choi, Gyeonggi-Do (KR); Suk Hoon Choi, Seoul (KR); Chang Hoon Choi, Seoul (KR)

( * ) Notice: Subject to any disclaimer, the term of this patent is extended or adjusted under 35 U.S.C. 154(b) by 178 days.

(21) Appl. No.: 14/904,507

(22) PCT Filed: Jan. 14, 2014

(86) PCT No.: PCT/KR2014/000393
§ 371 (c)(1),
(2) Date: Jan. 12, 2016

(87) PCT Pub. No.: WO2015/005553
PCT Pub. Date: Jan. 15, 2015

(65) Prior Publication Data
US 2016/0169870 A1  Jun. 16, 2016

(30) Foreign Application Priority Data
Jul. 12, 2013  (KR) ........................ 10-2013-0082060

(51) Int. Cl.
| G01N 33/48 | (2006.01) |
| G01N 33/50 | (2006.01) |
| C12N 5/00  | (2006.01) |
| G06G 7/58  | (2006.01) |
| A61K 35/00 | (2006.01) |

(52) U.S. Cl.
CPC ........... *G01N 33/5091* (2013.01); *C12N 5/00* (2013.01); *A61K 35/00* (2013.01); *G01N 2800/50* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

2009/0311664 A1   12/2009   Fong et al.

FOREIGN PATENT DOCUMENTS

| EP | 3095875 A1 | 11/2016 |
| EP | 3096141 A1 | 11/2016 |
| JP | 1975-020822 A | 3/1975 |
| JP | 1981-140253 A | 11/1981 |
| JP | H0412243 B2 | 3/1992 |
| JP | 2002223768 A | 8/2002 |
| JP | 2005-525124 A | 8/2005 |
| JP | 2008500514 A | 1/2008 |
| JP | 2011-510663 A | 4/2011 |
| JP | 2011163830 A | 8/2011 |
| JP | 2012111735 A | 6/2012 |
| KR | 20030033134 A | 5/2003 |
| WO | 0022432 A1 | 4/2000 |
| WO | 2006054296 A2 | 5/2006 |
| WO | 2009100029 A1 | 8/2009 |
| WO | 2012135844 A2 | 10/2012 |

OTHER PUBLICATIONS

Barry, O., et al., "Mechanisms of Cellular Activation by Platelet Microparticles", "Thrombosis and Haemostasis", Aug. 1999, pp. 794-800, vol. 82, No. 2.

Barry, O., et al., "Arachidonic Acid in Platelet Microparticles Up-regulates Cyclooxygenase-2-dependent Prostaglandin Formation via a Protein Kinase C/Mitogen-activated Protein Kinase-dependent Pathway", "The Journal of Biological Chemistry", Mar. 12, 1999, pp. 7545-7556, vol. 274, No. 11, Publisher: The American Society for Biochemistry and Moleular Biology.

English, D., et al., "Platelet-released phospholipids link haemostasis and angiogenesis", "Cardiovascular Research", 2001, pp. 588-599, vol. 49, No. 3, Publisher: Elsevier.

Morales-Ruiz, M., et al., "Sphingosine 1-Phosphate Activates AKT, Nitric Oxide Production, and Chemotaxis Through a Gi Protein/Phosphoinositide 3-Kinase Pathway in Endothelial Cells", "The Journal of Biological Chemistry", Jun. 1, 2001, pp. 19672-19677, vol. 276, No. 22.

Clayton, A., et al., "Cancer Exosomes Express CD39 and CD73 Which Suppress T Cells through Adnosine Production", "The Journal of Immunology", Jun. 15, 2011, pp. 676-683, vol. 187, Publisher: The American Association of Immunologists, Inc.

Deaglio, S., et al., "Adenosine generation catalyzed by CD39 and CD73 expressed on regulatory T cells mediates immune suppression", "The Journal of Experimental Medicine", Jun. 11, 2017, pp. 1257-1265, vol. 204, No. 6, Publisher: The Rockefeller University Press.

Sarma, R., et al., "Structure of Streptomyces erythraeus Lysozyme at 6 A Resolution", "J. Biochem.", 1979, pp. 1765-1771, vol. 86, No. 6.

*Primary Examiner* — Eric S Dejong

(74) *Attorney, Agent, or Firm* — Hultquist, PLLC; Steven J. Hultquist

(57) ABSTRACT

The present invention relates to a method for diagnosis of diseases using morphological characteristics of luterial which exists in blood. According to the present invention, morphological characteristics of luterial, such as the number, size or shape, and movement (nano-tracking speed) thereof change according to the kind and progress of a disease, and thus diagnosis and prognosis of a disease (particularly, cancer) can be effectively determined by observing and measuring the characteristics of luterial in the blood.

14 Claims, 43 Drawing Sheets

METHOD FOR DIAGNOSIS OF DISEASES USING MORPHOLOGICAL CHARACTERISTICS OF LUTERIAL

CROSS-REFERENCE TO RELATED APPLICATIONS

This application is a U.S. national phase under the provisions of 35 U.S.C. § 371 of International Patent Application No. PCT/KR14/00393 filed Jan. 14, 2014, which in turn claims priority of Korean Patent Application No. 10-2013-0082060 filed Jul. 12, 2013. The disclosures of such international patent application and Korean priority patent application are hereby incorporated herein by reference in their respective entireties, for all purposes.

TECHNICAL FIELD

The present invention relates to a method for diagnosis of diseases using morphological characteristics of luterial existing in body fluid, including blood, obtained from a patient.

BACKGROUND ART

A micromaterial in blood such as extracellular vesicles, and the like (altogether hereinafter referred to as EVs), has been recognized in the past as a material with no specific function. However, accumulating evidence suggest that EVs have various biological functions. For example, EVs derived from the platelets have been reported to stimulate a specific cell via selective expression of proteins (e.g. CD154, RANTES, PF-4) on the vesicular surface (Thromb. Haemost. (1999) 82:794; J. Biol. Chem. (1999) 274:7545), and biologically active lipids (e.g. HTET, arachidonic acid) from the platelet-derived EVs have been shown to have a certain effect on their target cells (J. Biol. Chem. (2001) 276:19672; Cardiovasc. Res. (2001) 49(5):88). Taken together, particular characteristics (e.g. size, surface antigens, determination of an origin cell, or payload) of EVs existing in a biological sample can provide information for a diagnosis, prognosis, or treatment of diseases, and, as such, a need for identifying a biological index capable of being utilized for detecting and treating diseases has been well recognized.

Meanwhile, cancer is an incurable disease which is the number one cause of death in most of the industrialized nations presently. A cancer cure rate is still low, and the number of death due to cancer has continuously increased and, in sequence, household burden and national medical expense burden have also significantly increased. Cancer is a disease where cells infinitely proliferate and interfere with functions of normal cells. The representative examples thereof include lung cancer, gastric cancer (GC), breast cancer (BRC) and colorectal cancer (CRC). However, cancer may substantially be generated in any tissue.

In the past, cancer was diagnosed based on external changes in biological tissue caused by growth of cancer cells, but recently, diagnosis and detection of cancer using a trace amount of biomolecules existing in biological tissues or cells such as blood, glycol chain, DNA, or the like, have been attempted. However, the most generally used method for diagnosis of cancer is via usage of a tissue sample obtained by biopsy or usage of an image. Among them, the biopsy has disadvantages in that it causes great pain in patients, requires high expense, and takes a long time for diagnosing cancer. In addition, in a case in which the patient actually has cancer, there is a risk of inducing cancer metastasis during a biopsy procedure, and in a case of a region at which tissue samples through the biopsy may not be obtained, it may be impossible to diagnose a disease before a suspected tissue sample is extracted through a surgical operation. In case of using the image, cancer is diagnosed based on an X-ray image, a nuclear magnetic resonance (NMR) image obtained using a contrast agent having a disease targeting material attached thereto, or the like. However, disadvantages of this type of diagnosis is that there is a probability of a wrong diagnosis depending on proficiency of a clinician or doctor reading the image, and its accuracy is significantly dependent on precision of a device obtaining the image. Further, even in a case of the most precise device, it is difficult to detect a tumor having a size of several mm or less, such that it may be difficult to detect the tumor at an early stage. In addition, since a patient or person with a risk is exposed to a high energy electromagnetic wave which may generate mutation of genes in the process, another disease may be induced. Another disadvantage is that the number of image diagnosis a patient may endure may be limited due to the risk of exposure.

As the biopsy for diagnosing cancer is accompanied by a long time, cost, discomfort, pain, and the like, a method capable of significantly decreasing the number of patients subject to unnecessary biopsy and accurately diagnosing cancer at an early stage is in much demand.

In this regard, the present inventors found that diseases may be diagnosed and predicted by observing morphological characteristics of luterial, which is a type of nanoparticle existing in body fluid of a patient, thereby completing the present invention.

DISCLOSURE

An object of the present invention is to provide a method for diagnosing diseases using morphological characteristics of luterial existing in body fluid of a patient.

In one aspect, the present invention provides a method of providing information for diagnosis and prognosis prediction of diseases via:

a) measurement by microscopy of at least one criterion from number, size (a diameter or an area), shape, membrane (eg. fascia, coat, film, and the like) formation and nano-tracking speed of luterial existing in body fluid of a patient; and b) comparison of the results measured or confirmed from the step a) with those of luterial of a normal person, normal luterial, or a red blood cell.

The present invention also provides a method of providing information for diagnosis and prognosis prediction of diseases via:

a) identifying a shape of luterial existing in body fluid of a patient using an electron microscopy;

b) classifying luterial according to a shape among the classes of a single shape, a fused shape, a multi-fused shape, and a fused shape in which a membrane is ruptured; and c) determining a stage of a disease based on the classification from the step b).

In another aspect, the present invention provides a method for diagnosis and prognosis prediction of diseases via:

a) measurement by microscopy of at least one criterion from number, size (a diameter or an area), shape, membrane (eg. fascia, coat, film, and the like) formation and nano-tracking speed of luterial existing in body fluid of a patient; and b) comparison of the results measured or confirmed from the step a) with those of luterial of a normal person, normal luterial, or a red blood cell.

The present invention also provides a method for diagnosis and prognosis prediction of diseases via:

a) identifying a shape of luterial existing in body fluid of a patient using an electron microscopy;

b) classifying luterial according to a shape among the classes of a single shape, a fused shape, a multi-fused shape, and a fused shape in which a membrane is ruptured; and c) determining a stage of a disease based on the classification from the step b).

Other features and embodiments of the present invention will become obvious from the following detailed description and the accompanying claims.

BRIEF DESCRIPTION OF DRAWINGS

FIGS. 7B to 7E: Stage 2 or 3).

FIGS. 8C/8D: middle stage; FIG. 8E: lymphogenous, peritoneal, and pericardial metastasis).

FIGS. 9B to 9D: middle stage).

FIG. 16B: shape progressive to rod-mass complex).

FIG. 22B: mass shape).

FIGS. 23B/23C: middle stage).

DETAILED DESCRIPTION OF THE EMBODIMENTS

Unless otherwise defined herein, all of the technical and scientific terms used in the present specification have the same meanings as those commonly understood by specialists in the skilled art to which the present invention pertains. Generally, nomenclature used in the present specification is well known and commonly used in the art.

As used herein, the term "luterial" denotes a nanoparticle (a living organism) having a size that ranges from the size of a virus to about 500 nm (during normal fission stage: 50 to 500 nm/during abnormal fusion stage: 800 nm or more) that are present in all animals, and such term was named by the present inventors. The luterial contains both DNA and RNA, and is distinguished from the exosome or microvesicle in view that the luterial has an adhesion property and motility.

Figure 1:
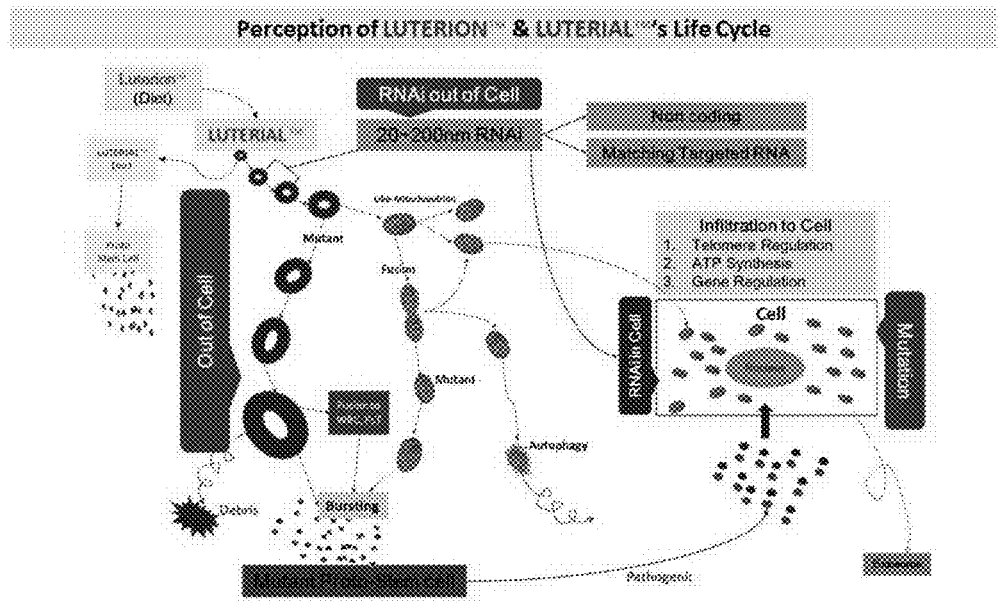
FIG. 1 schematically illustrates a life cycle of luterial.

In animals including human, the nanoparticle exists in blood, saliva, lymph, semen, vaginal mucus, breast milk (in particular, colostrum), umbilical cord blood, brain cells, the spinal cord, the bone marrow, and is referred to as "luterial". In addition, a nanoparticle existing in plants is referred to as "luterion", and an origin of the luterial found in animal blood, or the like, is hypothesized to be luterion derived from plants (FIG. 1).

The luterial may be referred to as a "pseudo-mitochondria", "mitochondria analog", or "proto-mitochondria" in view that the luterial is positively stained by Janus Green B, Rhodamine123, Mitotracker, Acridine Orange and DAPI, which are the known fluorescent-staining markers for mitochondria, the luterial appears to have a double membrane structure similar to mitochondria with less completed form of an inner cristae, and the luterial is observed in a range of the same laser wavelength as that of the mitochondria.

In animals including human, the luterial exists in blood, saliva, lymph, semen, vaginal mucus, breast milk (in particular, the colostrum), umbilical cord blood, brain cells, spinal cord, and bone marrow. In addition, in the cases of animals having a horn, the luterial exists in the horn.

The luterial is also expected to be associated with cell cycle and cell growth adjustment as well as signaling, cell differentiation and cell apoptosis, and among them, the present inventors found that the luterial is closely associated with diagnosis of cancer.

Normal luterial is expected to play a role of blocking growth of cancer cells and allowing cells to be recovered to a healthy immune system, and such role is performed via RNA interference (RNAi) through which a gene may be normalized. As such, in diseased states where an information system within RNA has deviated from a normal track to instruct production of a protein inducing diseases, luterial derived from a healthy person or animal intentionally interferes with this process to suppress progression of diseases such as cancer. In addition, since the luterial also participates in energy metabolism when it grows to a size of 200~500 nm, in case where the luterial does not perform its normal functions, a critical disorder in homeostasis and ATP production is induced, thereby causing diseases in respiration and energy metabolism.

Abnormal luterial that does not perform its normal function manifests different ecology and characteristics from the normal luterial such that the abnormal luterial has various sizes and shapes. More specifically, the normal luterial stops growing once it forms a double-spore, but the abnormal luterial found in blood of cancer patients or patients having a chronic disease manifests property of continuous growing similar to stem cells, such that the abnormal luterial has a size of 600 to 800 nm or more, and in some cases, grows to a size of 200 µm (200,000 nm) or more. Furthermore, the abnormal luterial manifests invasive behavior for growth in red blood cells, white blood cells, blood platelets, or the like, and aggregates with other luterials, similar to virus.

Meanwhile, the number, size (diameter or area), shape, coat formation and nano-tracking speed of the luterial are different depending on the presence or absence of a disease in an individual, such that it is possible to diagnose of the disease or to predict prognosis of the disease through one or a combination of these characteristics. This is appreciated from the fact that the number, size (diameter or area), shape, coating formation, and nano-tracking speed of luterial derived from a healthy person without a disease are different from those of luterial derived from a person with a disease. Such differences is caused by the presence or absence of mutation in the luterial, and hence the luterial derived from the person with the disease is hereinafter referred to as "mutant luterial" to distinguish it from the normal luterial derived from the healthy person.

Taken together, it is possible to diagnose the disease or to predict prognosis of the disease by observing the number and morphological or biochemical characteristics of the luterial existing in body fluid of a patient.

More specifically, in a patient, the number of luterials, particularly luterials having a size of 400 nm or less, is decreased as compared to a normal person, and in a severe state of disease, the number of luterial is decreased by 20 to 80%. Therefore, a case in which the number of luterial is equal to or less than 20% of that in the normal person may be suspected to have a tumor.

Further, if a mutant luterial with size (a long diameter) larger than 20 µm, it could be determined that the subject is suspected to have a tumor. Moreover, even in the case of finding the luterial with its long diameter being less than 20 µm, if a coat is formed outside the mutant luterial, then it could be determined that the subject is suspected to have a tumor. However, even in the presence of the luterial with its long diameter exceeding 20 µm, the absence of coat formation may indicate that the subject has a benign tumor.

Further, movement of the luterial derived from a patient is significantly decreased as compared to that derived from a normal person. The movement of the luterial may be quantified by measuring the nano-tracking speed.

Therefore, in one aspect, the present invention provides a method of providing information for diagnosis and prognosis prediction of diseases via:

a) measurement by microscopy of at least one criterion from number, size (a diameter or an area), shape, membrane (eg. fascia, coat, film, and the like) formation and nano-tracking speed of luterial existing in body fluid of a patient; and b) comparison of the results measured or confirmed from the step a) with those of luterial of a normal person, normal luterial, or a red blood cell.

In another aspect, the present invention relates to a method for diagnosis and prognosis prediction of diseases via:

a) measurement by microscopy of at least one criterion from number, size (a diameter or an area), shape, membrane (eg. fascia, coat, film, and the like) formation and nano-tracking speed of luterial existing in body fluid of a patient; and b) comparison of the results measured or confirmed from the step a) with those of luterial of a normal person, normal luterial, or a red blood cell.

The luterial observed in the present invention may be separated from the body fluid of the patient. As used herein, the term "body fluid of the patient" may include but not limited to blood, saliva, lymph, semen, vaginal mucus, breast milk (in particular, colostrum), umbilical cord blood, brain cells, spinal cord, or bone marrow. Most preferably, luterial derived from the blood may be used for the purpose of the present study. More specifically, it is possible to diagnose and predict prognosis of the disease by observing the luterial existing in a collected blood sample or separated from the blood using a microscope.

In the exemplary embodiment of the present invention, the luterial is obtained by a process including a first separation step of separating serum from blood; a second separation step of separating a precipitate that does not pass through a filter of various pore sizes with a diameter ranging from 100 nm to 2 mm from the separated serum; and a washing step of washing the separated precipitate.

In more detail, the first separation step may include collecting the blood from a patient and centrifuging the collected blood sample at 1200 to 5000 rpm for 5 to 15 minutes to obtain serum using a centrifuge. The second separation step may include a step of removing general EVs such as exosome from the serum using centrifugation to obtain a supernatant fraction; and a step of passing the obtained supernatant through the filter with various pore sizes with a diameter ranging from 100 nm to 2 mm to separate the precipitate that does not pass through the filter. Removal of the exosomes may be accompanied by, but not limited to, ExoQuick. The washing step may include a step of washing the serum separated from the precipitate (which may contain exosome) with normal saline. The washing step may further include a step of incubating in the ice (at 4° C. or less) after the washing.

In a case in which a long diameter of the luterial observed or photographed in step b) is 8 to 30 times larger than that of a red blood cell; or an area of the luterial observed or photographed in step b) is 8 to 30 times larger than that of the red blood cell, a disease may be determined to be a cancer suspected state.

When measuring the size of the luterial by observation or taking photographs, the luterial of a normal person has a size of 100 to 250 nm, but in a case of fatigue syndrome, the luterial has a size of 250 to 800 nm, and in the cases of diseases, the luterial has a size of 800 nm or more, maximally, several hundred μm (about 200 μm).

A case in which the number of luterial observed or photographed in step b) is 20% or less of the number of luterial of a normal person, and the size (diameter) thereof is 0.8 to 1 μm may be determined to be in a disease development suspected state, and a case in which the size thereof exceeds 20 μm may be determined to be in a cancer suspected state. In the case in which a coating is formed on the outside of mutant luterial, the mutant luterial may be determined to be a cancer marker regardless of the size thereof. Particularly, in a case in which the coating is formed and a flagellum (tentacle)-like structure is observed, such mutant luterial may be determined to be a marker for severe state of malignant tumor. The presence or absence of coating formation can be observed using a dark field microscope or electron microscope.

In step a), the shape of the luterial is observed or photographed, and in step b), a disease is diagnosed based on the observed or photographed shape of the luterial.

In step b), the shape of the luterial may be selected from the group consisting of a normal shape, a flagellum shape in which the luterial has a flagellum-like structure formed at an outer portion thereof, a mass (M) shape, a rod (L) shape, and a complex shape.

In the normal-shaped luterial, a ratio between a long diameter and a short diameter may be 1:1 to 3:1.

The mass-shape is an aggregate of luterials in a round form with the majority of its membrane being open, and a ratio between a long and short diameter thereof may be 3:1 to 5:1.

The rod-shape is an aggregate of luterials in a sharp and angular form with the majority of its membrane being closed, and a ratio between a long and short diameter thereof may be 5:1 to 12:1.

The rod-shape may be a rod-1 shape composed of a single circular or oval chain or a rod-2 shape composed of two or more single chains coupled to each other.

The complex shape may be a fused form of the rod shape and mass shape, of the rod shape and rod shape, or of the mass shape and mass shape.

In case where the shape of the luterials determined from observation or photographs in step b) is the rod shape, such luterial may function as a marker for lung cancer, breast cancer, pancreatic cancer, common bile duct cancer, pleural mesothelioma, thyroid cancer, ovarian cancer, biliary track cancer, prostate cancer, or lymphoblastic blood cancer development. In case where the shape determined is the mass shape, the luterial may function as a marker for liver cancer, angiosarcoma of liver, colorectal cancer, uterine cancer, gastric cancer (stomach cancer), kidney cancer, rectal cancer, or myeloid blood cancer development. In case where the shape determined is the complex shape, the luterial may function as a marker for severe leukemia or metastasis suspected state. In case where the shape determined is the flagellum shape, the luterial may function as a marker for an end-stage tumor suspected state.

Furthermore, the primary site of cancer may be tracked from the shape of the mutant luterial. In case where the luterial has the rod shape, the primary site of cancer may be determined to be the lung, breast, pancreas, bile duct, thyroid, ovary, biliary tract, prostate or lymphoblastic blood. In case where the luterial has the mass shape, the primary site of cancer may be determined to be liver, large intestine, uterus, digestive organ (stomach), kidney, rectum or myeloid blood. Further, in case where the luterial has the complex shape, if it progresses from the rod shape to the mass shape, the primary site of cancer is the same as that in the rod-shaped luterial, and if it progresses from the mass shape to the rod shape, the primary site of cancer is the same as that in the mass-shaped luterial.

According to the present invention, stage 1 to 4 cancer suspected states may be determined by measuring the nano-tracking speed indicating motility of the luterial. A case in which the nano-tracking speed of the luterial measured by observation or photograph in step b) is 8.0 to 11 µm/sec may be determined to be in a stage-1 cancer suspected state. A case in which the nano-tracking speed is 2.5 to 8.0 µm/sec may be determined to be in a stage-2 cancer suspected state. A case in which the nano-tracking speed is 0.5 to 2.5 µm/sec may be determined to be in a stage-3 cancer suspected state. A case in which the nano-tracking speed is less than 0.5 µm/sec may be determined to be in a stage-4 cancer suspected state.

In one aspect, the present invention relates to a method of providing information for diagnosis and prognosis prediction of diseases via:

a) identifying a shape of luterial existing in body fluid of a patient using an electron microscopy;

b) classifying luterial according to a shape among the classes of a single shape, a fused shape, a multi-fused shape, and a fused shape in which a membrane is ruptured; and c) determining a stage of a disease based on the classification from the step b).

In another aspect, the present invention relates to a method for diagnosis and prognosis prediction of diseases via:

a) identifying a shape of luterial existing in body fluid of a patient using an electron microscopy;

b) classifying luterial according to a shape among the classes of a single shape, a fused shape, a multi-fused shape, and a fused shape in which a membrane is ruptured; and c) determining a stage of a disease based on the classification from the step b).

The luterial derived from the blood can be confirmed via positive staining with one or more dyes selected from the group consisting of Rhodamine123, Mitotracker, Acridine Orange, DAPI and Janus Green B, and appears to have a double membrane structure with a cristae that can be confirmed through an electron microscopy.

In step c), a case in which the shape of the luterial determined by observation or photograph coincides with 80 to 100% of the single luterial form may be determined to be normal. A case in which its shape coincides with 80 to 100% with the fused shape may be determined to be in a disease suspected state. A case in which its shape coincides with 80 to 100% of the multi-fused shape may be determined to be in a tumor suspected state. In case where its shape coincides with 80 to 100% of the fused shape and its membrane is ruptured, the subject may be determined to be in a severe tumor suspected state.

Hereinafter, the present invention will be described in detail through the Examples. However, these Examples are only to illustrate the present invention, and those skilled in the art will appreciate that these Examples are not to be construed as limiting a scope of the present invention.

Example 1: Separation of Luterial Derived from Blood

A serum was separated by centrifuging 250 µl of blood collected from an end-stage non-small cell lung cancer patient at 1600 rpm for 10 minutes. After adding 63 µl of ExoQuick (SBI Corp.) to the serum and performing centrifugation at 3000 rpm for 15 minutes, the resultant was additionally maintained for 15 minutes, and then, an upper layer that did not react with ExoQuick was separated. The separated upper layer (supernatant) was filtered with a microfilter (100 nm), thereby separating a precipitate that did not pass through the microfilter. The resultant was washed with normal saline several times, and the icing (4° C. or less) was maintained, thereby separating luterial corresponding to a micromaterial.

Example 2: Microscope Observation and Luterial Confirmation

The luterial separated in Example 1 may be observed using a confocal laser scanning microscope (FIG. 2A), and stained with Rhodamine 123 and then confirmed using the confocal laser scanning microscope (FIG. 2B), and a positive reaction of the luterial stained with Janus Green B was confirmed using an optical microscope.

Figure 2A:
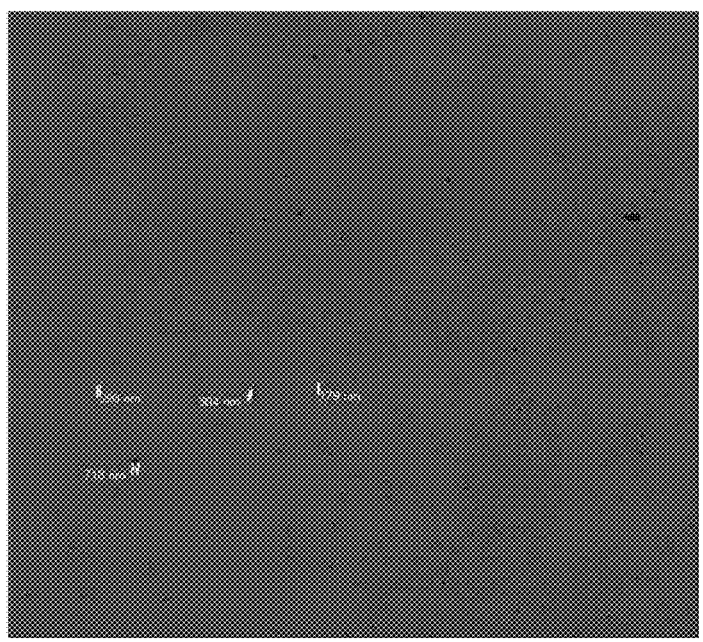
FIG. 2A is a photograph of luterial derived from blood of an end-stage non-small cell lung cancer patient, photographed using a confocal laser scanning microscope.
Figure 2B:
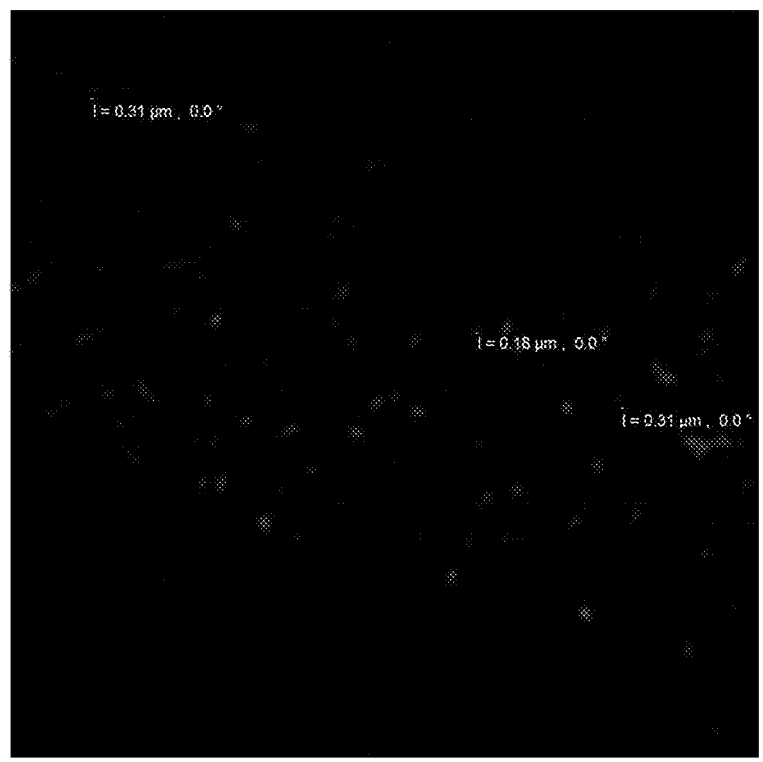
FIG. 2B is a confocal laser scanning microscope photograph of luterial derived from blood of an end-stage non-small cell lung cancer patient obtained after fluorescent-staining with Rhodamine 123.
Figure 2C:
FIG. 2C is a photograph of luterial derived from blood of an end-stage non-small cell lung cancer patient, photographed using an electron microscope.

In addition, the separated luterial was manufactured in a form of an electronic microscope sample to thereby be observed (FIG. 2C). After fixing a blood cell with MICA, a membrane was stripped using a probe, thereby making it possible to confirm DNA and RNA (using atomic force microscope). A fixing agent Cell-Tack BD (Bioscience Corp.) or glutaraldehyde/poly-L-lysine may be used instead of MICA. After 5 minutes from application of Rhodamine 123 (fluorescent-staining agent), the luterial was washed and then, observed using an orange filter (a filter having a wavelength band of 506 nm to 520 nm) in dark field microscope, thereby confirming that a green color was observed.

FIGS. 2A to 2C are photographs of the luterial separated in Example 1, and in a case of fluorescent-staining of the luterial with Rhodamine 123 as illustrated in FIG. 2B, the luterial is specifically stained, and observed by the confocal laser scanning microscope. The luterial may be specifically stained with Janus Green B, and observed by an optical microscope. Staining of the luterial may be confirmed by the Mitotracker, Acridine Orange, and DAPI, which are fluorescent-staining agents.

The luterial illustrated in FIG. 2A has a diameter of at most 718 nm, that is, 0.718 µm, and it was confirmed that a coating was formed on the outside as illustrated in FIG. 2C. Actually, a patient corresponding to an experimental group was diagnosed with end-stage non-small cell lung cancer. Therefore, in the method for diagnosis and prognosis prediction of diseases according to the present invention, a case in which the diameter of the observed or photographed luterial is 0.5 µm or more and the coating is formed on the outside may be determined to be in a cancer suspected state.

FIG. 2C is an electron microscope photograph of the luterial, and it was confirmed that the luterial used to the method for diagnosis and prognosis prediction of diseases according to the present invention had a double membrane structure in which the coating was formed on the outside and an internal cristae structure was not completed.

Example 3: Measurement of Diameter of Luterial Derived from Various Subjects (Electron Microscope)

After separating luterials from bloods of various subjects (30 persons) from a normal person to an end-stage cancer patient by the same method as in Example 1, a diameter of the luterial was measured using an electron microscope.

Figure 3:
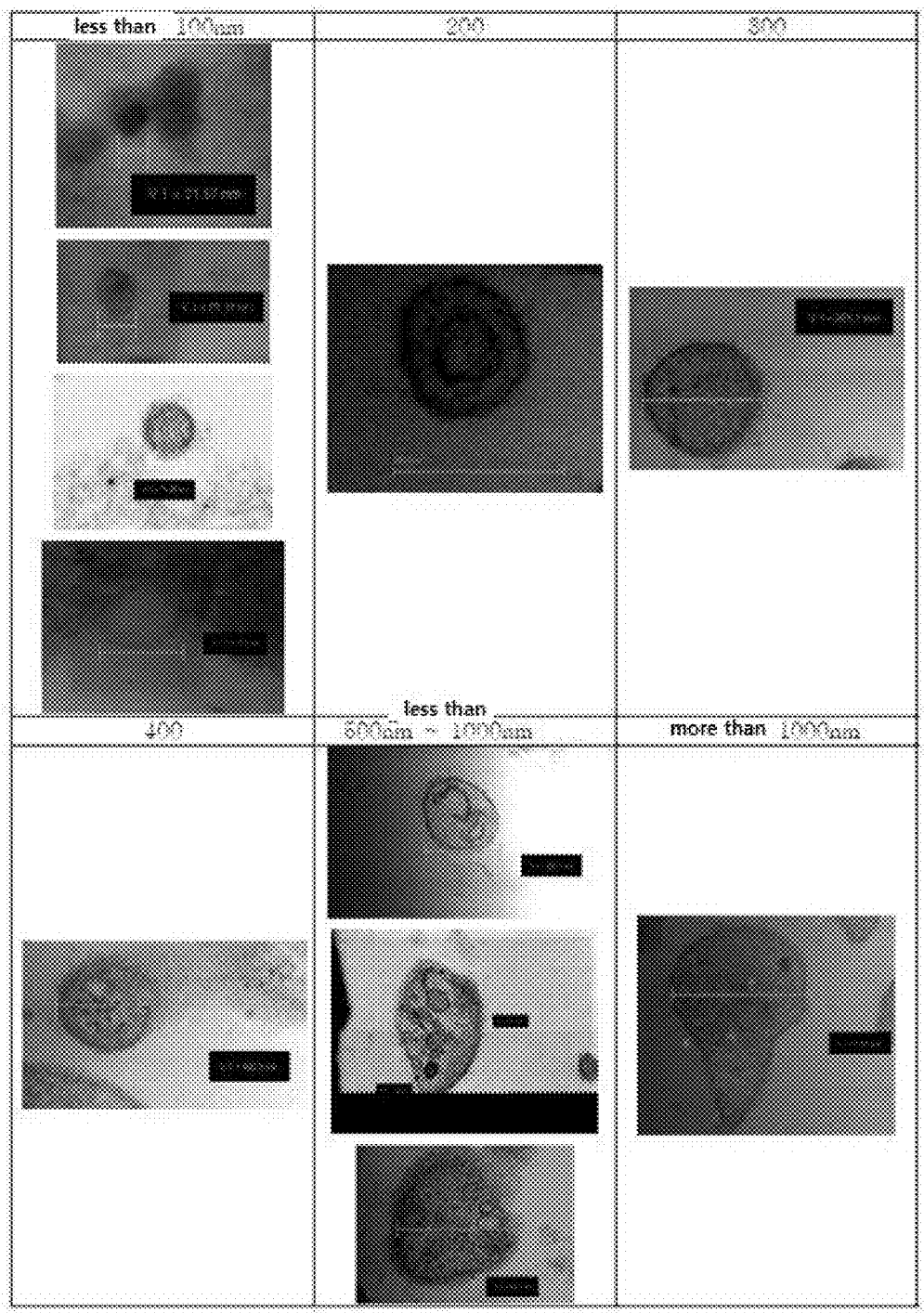
FIG. 3 illustrates photographs of luterial derived from blood, photographed using the electron microscope and arranged by diameter (from 100 to 1000 nm or more).

FIG. 3 illustrates photographs of the observed luterials, arranged by diameter (from 100 to 1 µm). The fused or mutated luterial was found at a diameter of 450 nm or more (substantially 800 nm or more), and in the most of them, diseases were diagnosed. Therefore, in the method for diagnosis and prognosis prediction of diseases according to the present invention, a case in which the diameter of the luterial observed or photographed using a microscope is 800 nm, that is, 0.8 μm or more, may be determined to be in a disease development suspected state (which may also be observed at a diameter of 0.45 μm with an electron microscope or atomic force microscope). The maximum size observed with the microscope was 200 μm, but the maximum size may be increased depending on a patient.

A plurality of luterials (FIG. 3) having a diameter of 800 nm (0.8 μm) and forming the coating were found in the blood derived from the cancer patient. Therefore, in the method for diagnosis and prognosis prediction of diseases according to the present invention, in a case in which the diameter of the luterial observed or photographed using the microscope is 0.8 μm or more and the coating is formed, a disease may be determined to be a cancer suspected state.

Example 4: Microscopic Observation of Luterial Derived from Blood of Normal Person After blood collected from a normal person without symptoms of diseases was smeared on a slide glass and covered with a cover glass, a drop of oil for a dark-field was added thereto, and the blood was observed using a dark field microscope (Nikon Eclipse Ni (1000×)) at a magnification of 1000×.

Figure 4A:
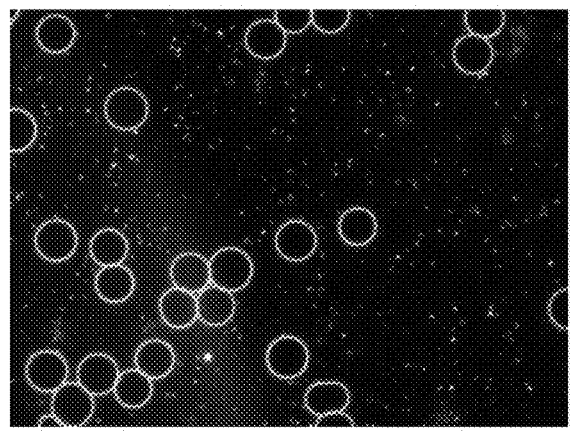
FIG. 4A is a photograph of luterial (step 1) in blood of a normal person, photographed using a dark field microscope.

As a result, as illustrated in FIG. 4A, luterial indicated as twinkling points was observed. A circular material indicates a red blood cell, and the luterial derived from the normal person was observed to be significantly small as compared to the red blood cell.

Example 5: Diagnosis and Prognosis Prediction of Disease Depending on Diameter of Luterial Luterial was separated from bloods collected from stage-1, stage-2, stage-3, and stage-4 cancer patients (Each stage: 15 patients) by the same method as in Example 1.

After the separated luterial was put into a buffer solution and stained with Rhodamine 123, a diameter thereof was measured using a confocal laser scanning microscope. An observation rate of luterial variant having a diameter of 2 μm or more, that is, mutant luterial was as follows.

TABLE 1

| | rate of mutant luterial with long diameter of 2 μm or more observed in experimental groups |
|---|---|
| Cancer stage 1 | 72.2% |
| Cancer stage 2 | 83.5% |
| Cancer stage 3 | 91.3% |
| Cancer stage 4 | 93.6% |

As a stage of cancer increased from an early stage to an end stage, the mutant luterial having a diameter of 2 μm or more increased. In about 94% of the stage-4 cancer patients, the mutant luterial having a diameter of 2 μm or more was found, and the maximum size was observed to be 200 μm or more. Further, in the stage-1 to stage-3 cancer patients, an observation rate of mutant luterial having a diameter of 0.5 to 5 μm was high. Further, in the stage-4 cancer patients corresponding to end-stage cancer patients, an observation rate of mutant luterial having a diameter of 5 μm or more was high.

Therefore, in the method for diagnosis and prognosis prediction of diseases according to the present invention, a case in which the diameter of the luterial observed or photographed using the microscope is 1.0 to 200 μm may be determined to be in a cancer suspected state, and a case in which the diameter of the luterial is 20 μm or more and a coating is formed may be determined to be in a cancer suspected state.

Example 6: Diagnosis and Prognosis Prediction of Disease Depending on Shape of Luterial After bloods collected from a normal person, a patient with gene-methylation abnormalities, a patient with gene mutation, a patient with tumor-associated gene mutation, and a patient with tumor-associated gene complex mutation (an end-stage prostate cancer patient) were smeared on a slide glass and covered with a cover glass, a drop of oil for a dark-field was added thereto, and the bloods were observed using a dark field microscope (Nikon Eclipse Ni (1000×)) at a magnification of 1000×.

In addition, an observation rate of the flagellum-shaped luterial to the observed luterial was calculated with respect to stage-1 to stage-4 cancer patients among the patients in experimental groups.

TABLE 2

| | rate of flagellum-shaped luterial observed in experimental groups |
|---|---|
| Cancer stage 1 | 2.3% |
| Cancer stage 2 | 7.2% |
| Cancer stage 3 | 13.6% |
| Cancer stage 4 | 99.1% |

The shapes of the luterial photographed according to Example 6 are classified into 8 steps (from step 2 to step 9) according to the degree of seriousness of the disease, and illustrated in FIGS. 4B to 4I, and step 1 is illustrated in FIG. 4A.

Figure 4B:
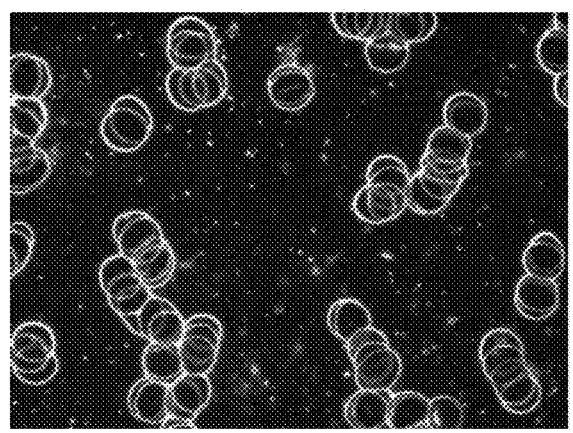
FIG. 4B is a photograph of luterial (step 2) of blood of a normal person, photographed using the dark field microscope.
Figure 4C:
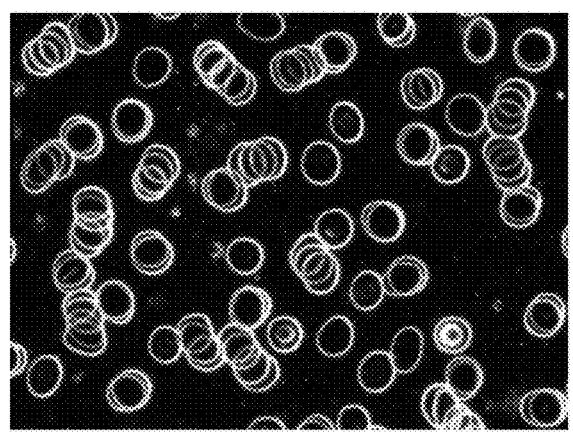
FIG. 4C is a photograph of luterial (step 3) of blood of a normal person, photographed using the dark field microscope.
Figure 4D:
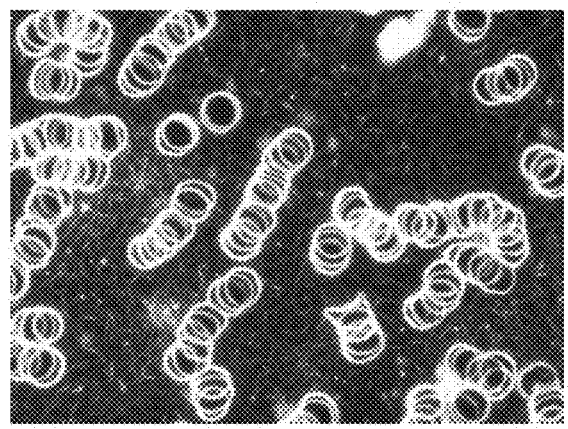
FIG. 4D is a photograph of luterial (step 4) of blood of a patient with a chromosomal methylation abnormalities, photographed using the dark field microscope.
Figure 4E:
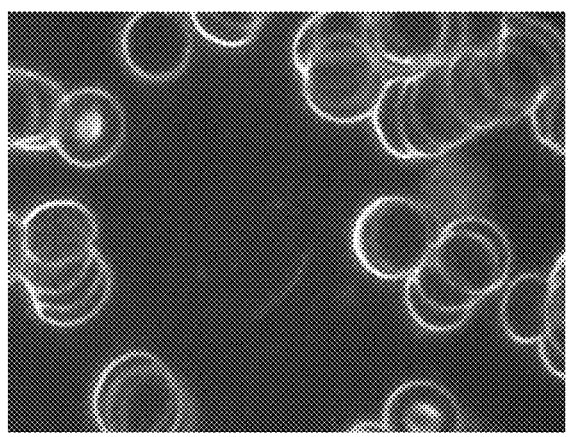
FIG. 4E is a photograph of luterial (step 5) of blood of a patient with gene mutation, photographed using the dark field microscope.
Figure 4F:
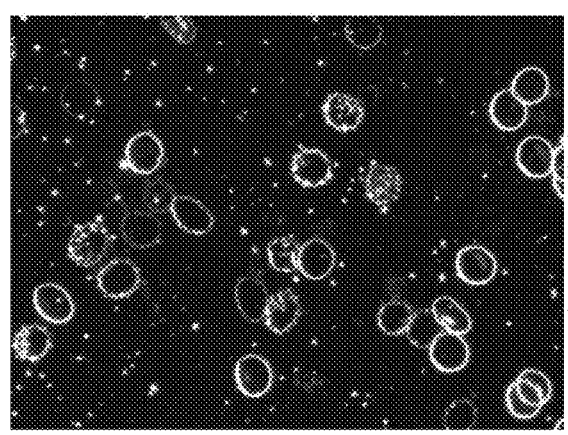
FIG. 4F is a photograph of luterial (step 6) of blood of a patient with gene mutation, photographed using the dark field microscope.
Figure 4G:
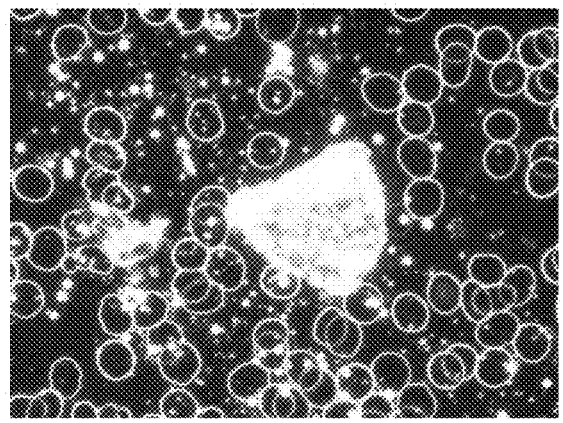
FIG. 4G is a photograph of luterial (step 7) of blood of a patient with tumor-associated gene mutation, photographed using the dark field microscope.
Figure 4H:
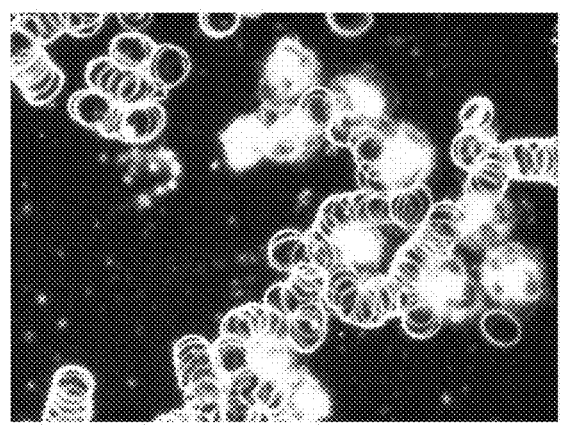
FIG. 4H is a photograph of luterial (step 8) of blood of a patient with tumor-associated gene complex mutation, photographed using the dark field microscope.
Figure 4I:
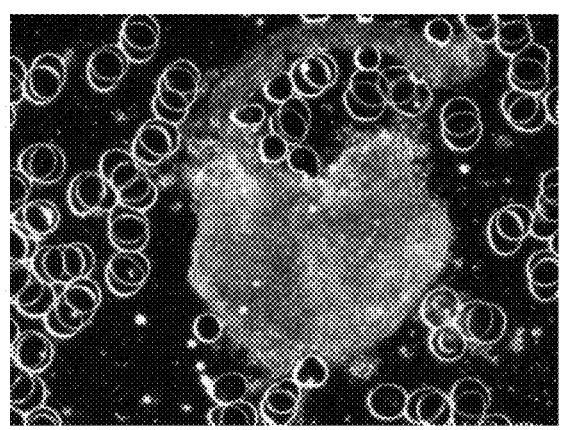
FIG. 4I is a photograph of luterial (step 9) of blood derived from an end-stage cancer patient, photographed using the dark field microscope.

FIGS. 4B and 4C are photographs of luterial (step 2 and step 3) derived from bloods of normal persons, FIG. 4D is a photograph of luterial (step 4) derived from blood of a patient with a methylation abnormalities, FIGS. 4E and 4F are photographs of luterial (step 5 and step 6) derived bloods of patients with gene mutation, FIG. 4G is a photograph of luterial (step 7) derived from blood of a patient with tumor-associated gene mutation, FIG. 4H is a photograph of luterial (step 8) derived from blood of a patient with tumor-associated gene complex mutation, and FIG. 4I is a photograph of luterial (step 9) derived from blood derived from a patient with tumor-associated gene complex mutation (an end-stage prostate cancer patient). In FIGS. 4B to 4I, circular materials are red blood cells or white blood cells.

First, twinkling silver-colored micromaterials except for the circular materials are the luterial in FIGS. 4B and 4C. The luterial derived from the normal person had a smaller size than that of the red blood cell, and a cluster of luterials with fused or deformed shape was not found.

FIG. 4D is the photograph of the luterial derived from the blood of the patient with chromosome methylation abnormalities, and at the time of comparing the luterial (classification step 3) of FIG. 4C, a size was increased, but a cluster of luterials with fused or deformed shape was not found yet.

FIGS. 4E and 4F are the photographs of the luterial derived from blood of the patients with gene mutation, and particularly, in classification step 6 of FIG. 4F, it may be appreciated that fusion of the luterial proceeded as compared to the classification step 4 of FIG. 4D. In the patient with gene mutation of FIGS. 4E and 4F, mutation of the tumor-associated gene did not occur yet.

FIG. 4G is the photograph of the luterial (classification step 7) derived from the blood of the patient of which mutation was generated in some of tumor-associated genes, and mutant luterial (mass-shaped luterial) cluster (a central silver colored material) having an absolutely large size equal to or more than 20 times larger than a size of the red blood cell was observed as compared to FIGS. 4E and 4F.

FIG. 4H is the photograph of the luterial (classification step 8) derived from the blood of the patient of which complex mutation was generated in tumor-associated genes, and it was observed that a size of the luterial was significantly increased as compared to classification step 7, and the luterial had a rod shape.

FIG. 4I is the photograph of the luterial (step 9) derived from the blood of the end-stage cancer patient, and it was observed that the luterial had the flagellum shape, unlike step 8. The patient in which the mutant luterial provided with the flagellum was observed was classified as an end-stage cancer patient, and a survival time of the cancer patient having the flagellum-shaped luterial was 1 to 4 months. Further, in a case in which a flagellum (300 nm or more) was released as illustrated in FIG. 4I, the survival time was within 2 months.

As a result of microscopic observation according to Example 6, it may be confirmed that the luterial derived from blood may have the normal shape, the flagellum shape, the mass shape, the rod shape, and the complex shape.

The normal-shaped luterial, which is luterial having a shape in which there was no deformation such as separate fusion, bursting, or the like, in the observed or photographed luterial and a ratio between a long diameter and a short diameter of the luterial is 1:1 to 3:1, was indicated as a small point at the time of microscopic observation. The normal-shaped luterial was illustrated in FIGS. 4A to 4C. In the method for diagnosis and prognosis prediction of diseases according to the present invention, a case in which the shape of the observed or photographed luterial coincides with 80 to 100% of the normal shape may be determined to be normal.

The flagellum-shaped luterial, which is luterial having a shape in which the observed or photographed luterial was deformed or fused to thereby be provided with a flagellum at an outer portion thereof, was observed in FIG. 4I. As the stage of cancer approaches the end-stage, an observation rate of the flagellum-shaped luterial was rapidly increased, and in stage-4 cancer, the observation rate was 99.1%, such that in most of the stage-4 cancer patients, the flagellum-shaped luterial was observed. In the method for diagnosis and prognosis prediction of diseases according to the present invention, a case in which the shape of the observed or photographed luterial coincides with 80 to 100% of the flagellum shape may be determined to be in an end-stage tumor suspected state. A survival time of the patient diagnosed with the end-stage tumor was 1 to 4 months. Particularly, in a case of the flagellum-shaped luterial, long-term survival of the patient is impossible.

Figure 5:
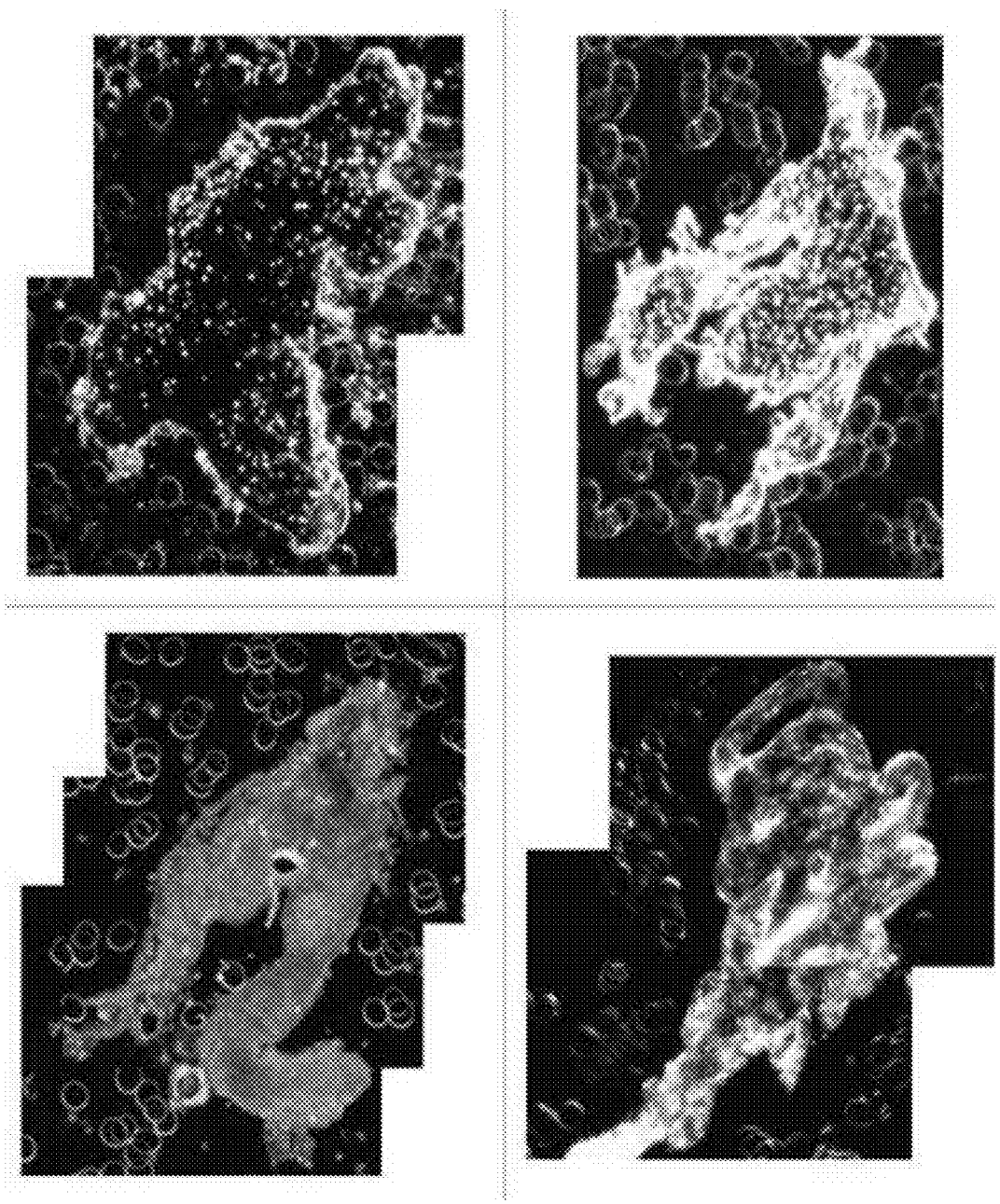
FIG. 5 is a photograph of mass-shaped luterial, photographed using the dark field microscope.

The mass (M)-shaped luterial, which is luterial having a shape in which the observed or photographed luterial is burst or fused to thereby have a size and shape changed from a normal-shaped luterial, has an irregular volume shape in which difference between a long diameter and a short diameter thereof is not large. Preferably, a ratio between the long diameter and the short diameter thereof may be 3:1 to 5:1. FIGS. 4G and 5 are photographs of the mass-shaped luterial, photographed using the dark field microscope according to Example 6, and mass-shaped luterial having various shapes is observed. A disease may be determined by comparing a shape of observed or photographed luterial using the mass-shaped luterial as a control group.

Figure 6:
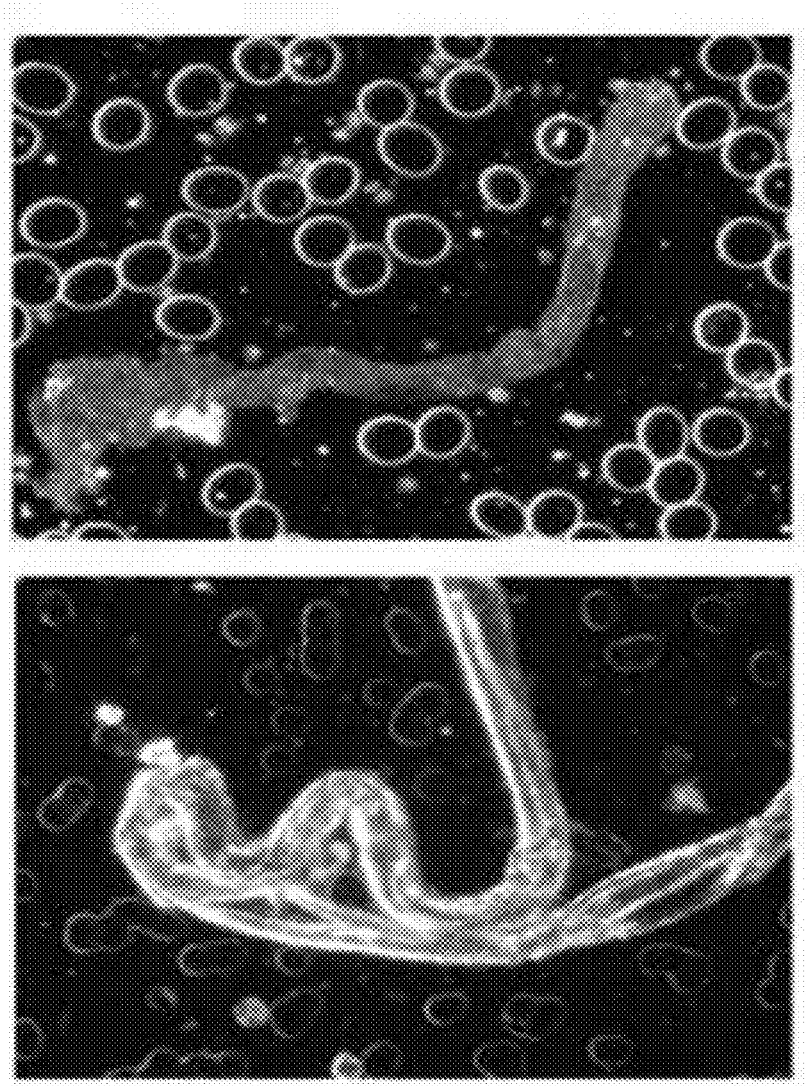
FIG. 6 is a photograph of rod-shaped luterial, photographed using the dark field microscope.

The rod (L)-shaped luterial is luterial having a shape in which the observed or photographed luterial burst, was deformed, or fused to thereby have a rod shape, and a length difference between a long diameter and a short diameter is larger than that of the mass-shaped luterial. Preferably, a ratio between the long diameter and the short diameter may be 5:1 to 12:1. The rod-shaped luterial is observed in various shapes as illustrated in FIG. 6. The rod-shaped luterial may include luterial having the rod 1 shape composed of a circular or oval single chain, and luterial having the rod 2 shape composed of two or more single chains coupled to each other. The rod 1-shaped luterial is single luterial having a rod shape, and the rod 1 shape is formed by bursting and/or deformation. The rod 2-shaped luterial is formed by two or more luterials coupled to each other to thereby have a rod shape, and the rod 2 shape is formed by at least one of bursting, deformation, and fusion.

The flagellum-shaped luterial may be included in the rod-shaped luterial in a large category, but there is a difference in that a flagellum protrudes. Therefore, after determining whether or not the luterial has the rod shape, it is possible to determine whether or not the luterial has the flagellum shape.

The complex shape may be a fused shape of the rod shape and the mass shape. In a case in which a portion of luterials formed integrally with each other has a rod shape and another portion thereof has a mass shape, the luterial may be referred to as the complex-shaped luterial.

Example 7: Diagnosis and Prognosis Prediction of Diseases Depending on Shape of Luterial Derived from Various Kinds of Cancer Patients Bloods collected from patients diagnosed with various kinds of cancer (Table 3) or luterials obtained from the bloods by the same method as in Example 1 were observed.

After the blood sample or luterial was put into a buffer solution to be smeared onto a slide glass and covered with a cover glass, a drop of oil for a dark-field was added thereto, and the blood or luterial was observed using a dark field microscope (Nikon Eclipse Ni (1000×)) and a confocal scanning microscope.

As a result, in the cases of lung cancer, breast cancer, pancreatic cancer, common bile duct cancer, pleural mesothelioma, thyroid cancer, ovarian cancer, biliary track cancer, prostate cancer, and acute lymphoblastic leukemia, the rod (L)-shaped luterial was observed as illustrated in Table 4.

Further, in the cases of liver cancer, angiosarcoma of liver, colorectal cancer, uterine cancer, gastric cancer (stomach cancer), rectal cancer, or acute myeloid leukemia, the mass (M)-shaped luterial was observed.

In the cancer patient with metastasis, the complex-shaped luterial in which the mass-shaped luterial and the rod-shaped luterial are combined was observed, and in the end-stage cancer patient, the flagellum-shaped luterial was observed as illustrated in FIG. 4I.

In the case in which the shape of the luterial progressed from the rod shape to the rod-mass (L-M) shape, it may be determined that an original cancer development site was the same as that in the rod (L)-shaped luterial, but metastasis was progressive. Further, in the case in which the shape of the luterial progressed from the mass shape to the mass-rod (M-L) shape, it may be determined that an original cancer development site was the same as that in the mass (M)-shaped luterial, but metastasis was progressive.

TABLE 3

Figure 7A:
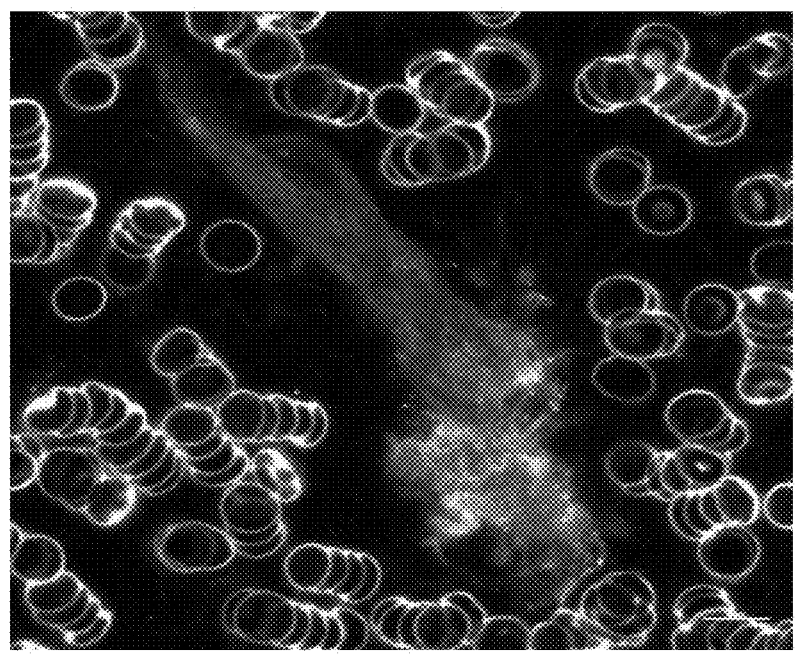
FIGS. 7A to 7E are photographs of luterial derived from lung cancer patients, photographed using the dark field microscope (FIG. 7A: early stage.
Figure 7B:
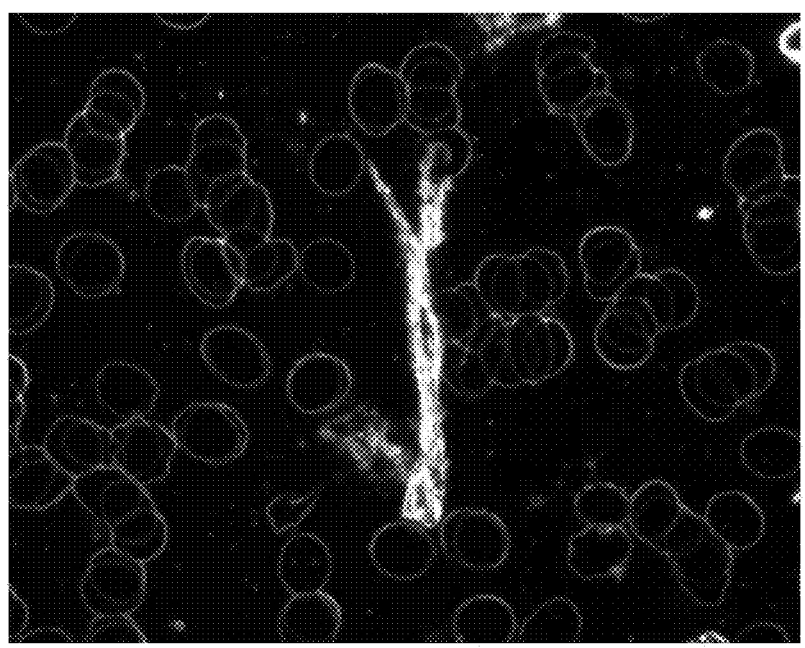
Figure 7C:
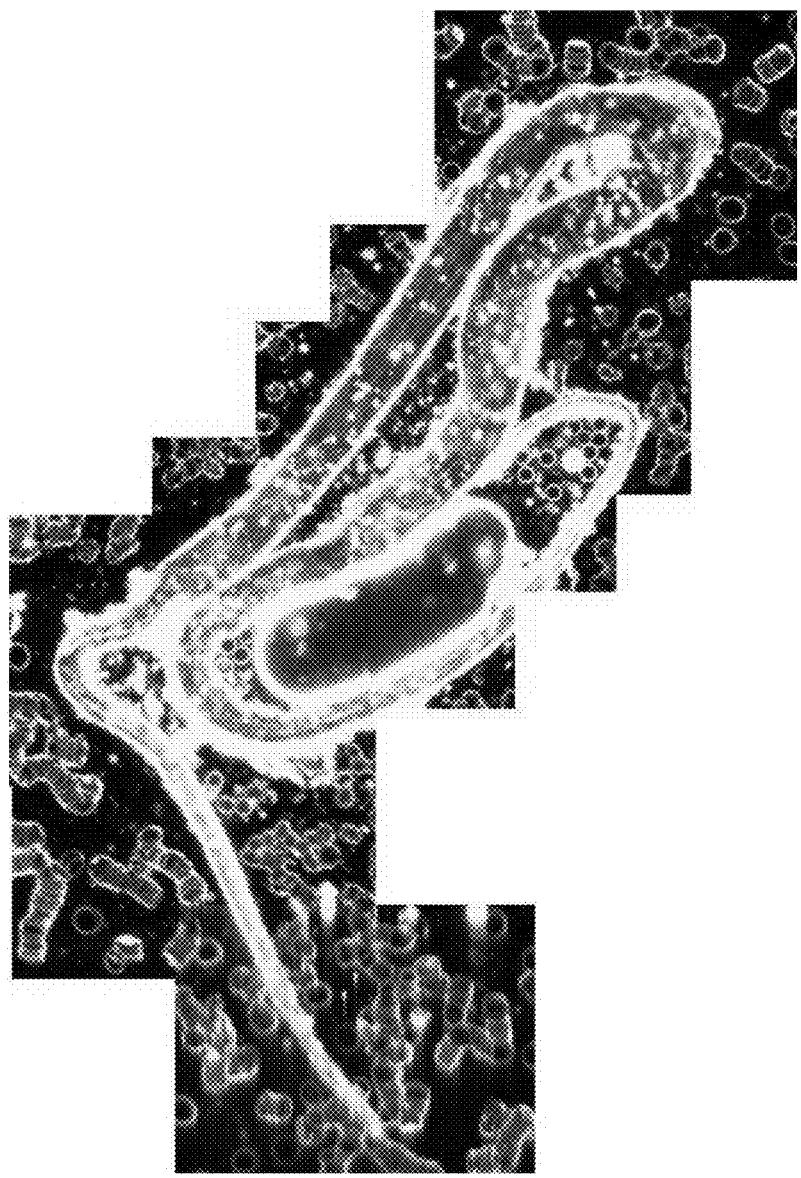
Figure 7D:
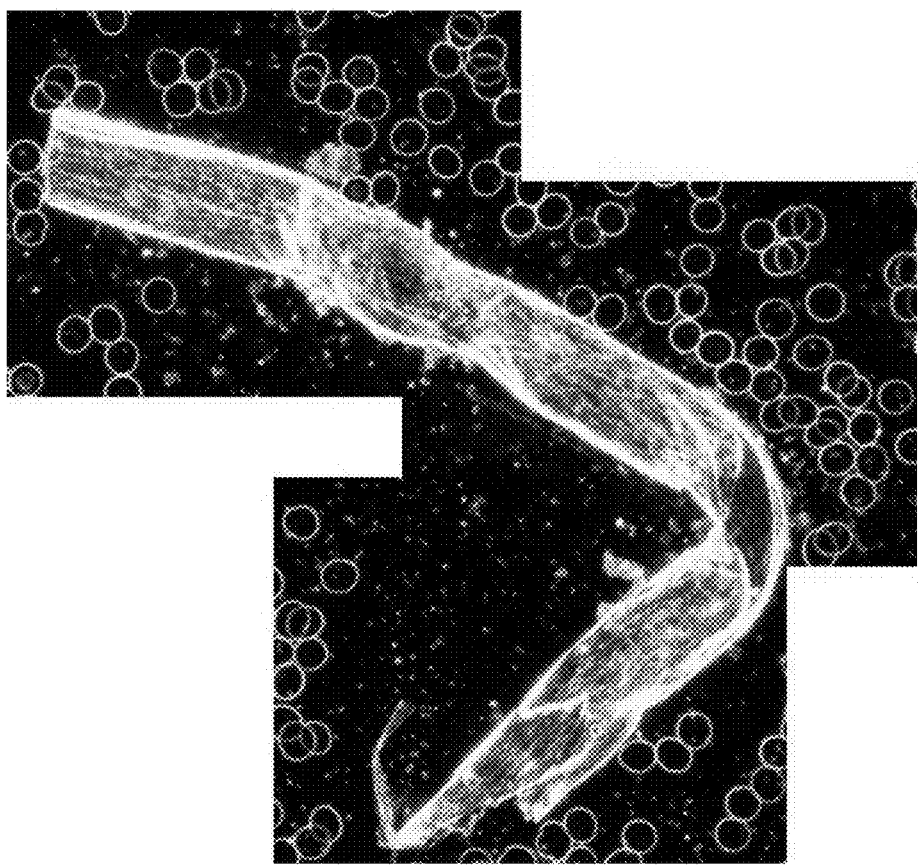
Figure 7E:
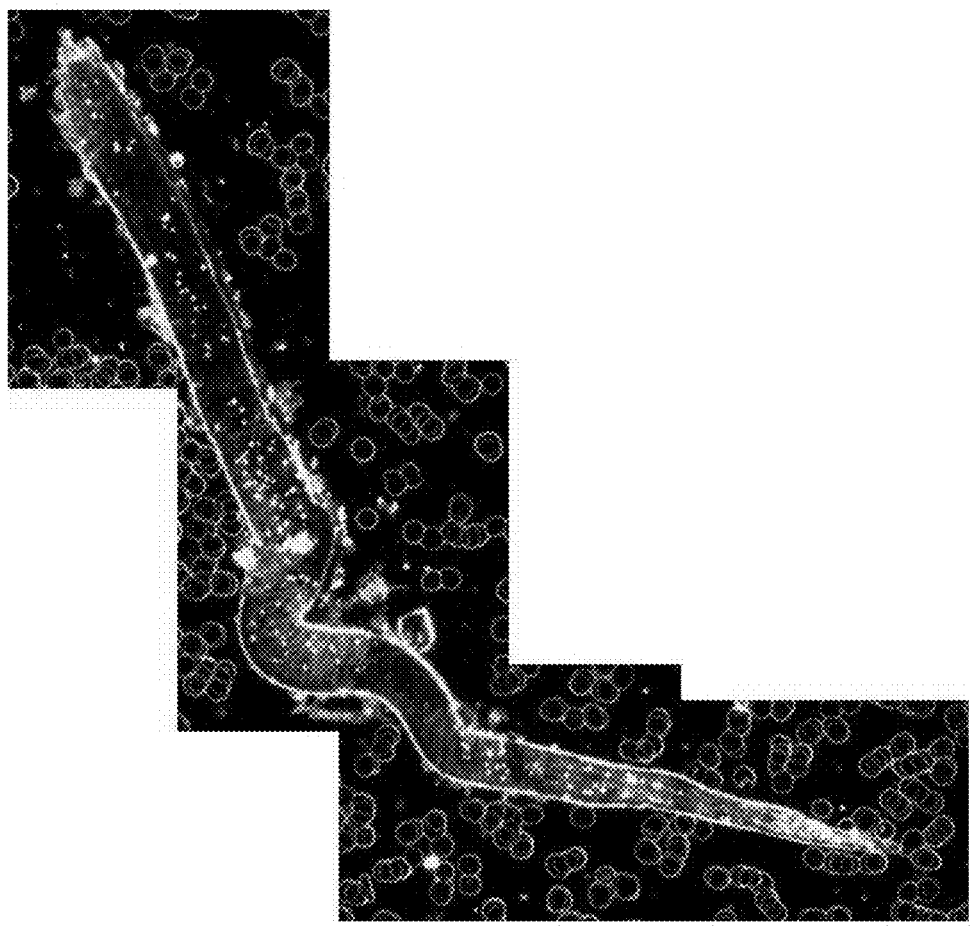
Figure 8A:
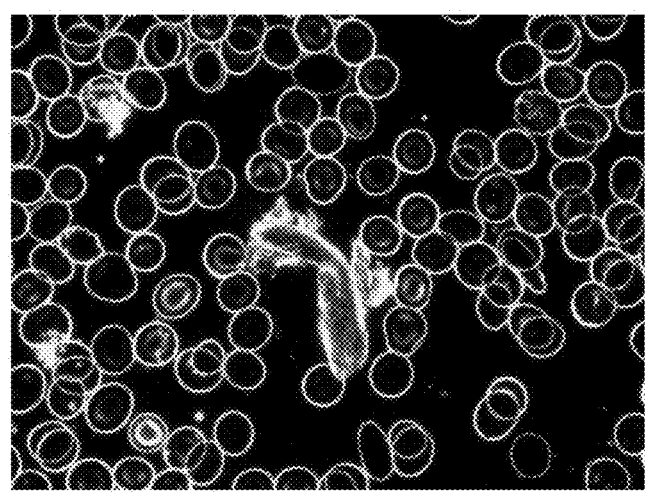
FIGS. 8A to 8E are photographs of luterial derived from breast cancer patients, photographed using the dark field microscope (FIGS. 8A/8B: early stage.
Figure 8B:
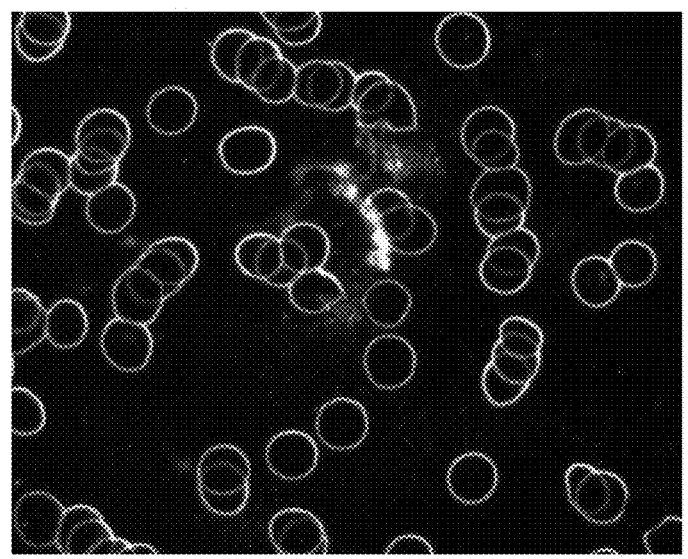
Figure 8C:
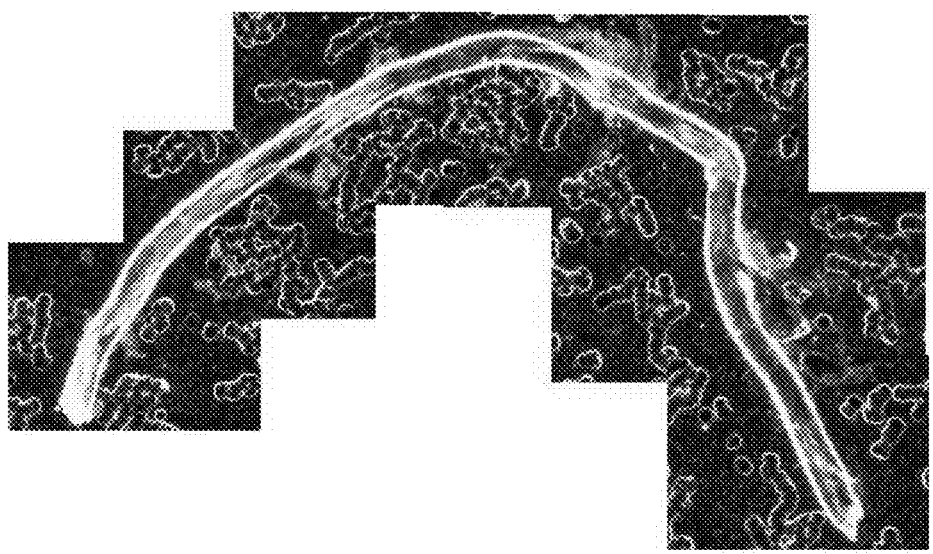
Figure 8D:
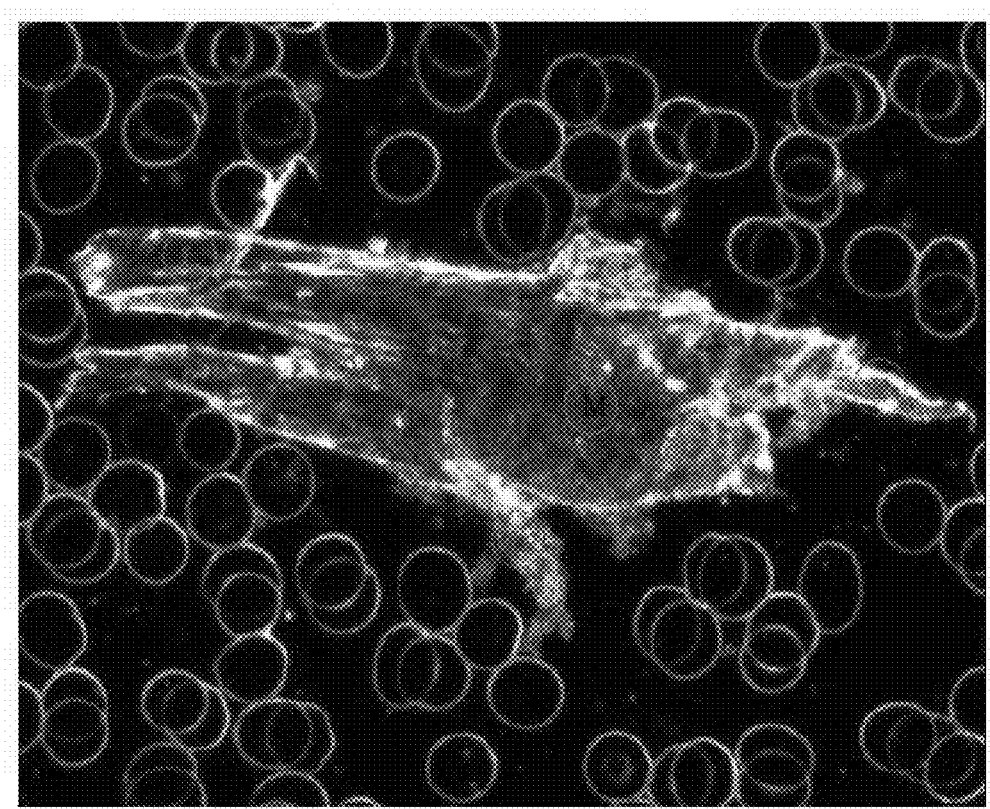
Figure 8E:
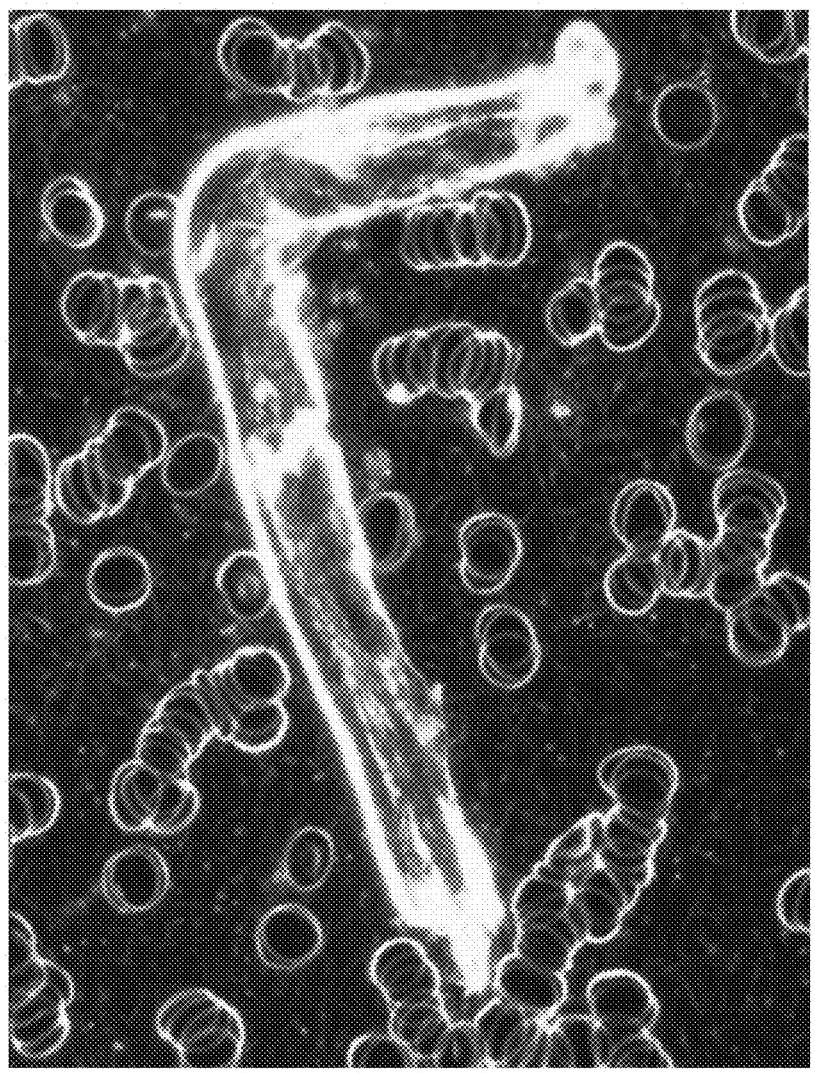
Figure 9A:
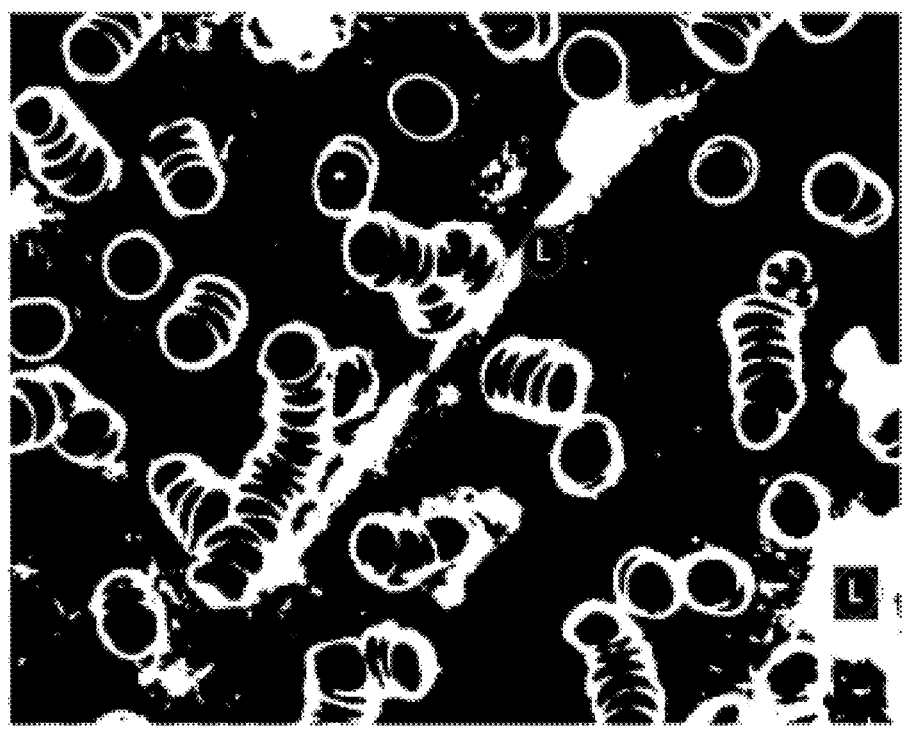
FIGS. 9A to 9D are photographs of luterial derived from pancreatic cancer patients, photographed using the dark field microscope (FIG. 9A: early stage.
Figure 9B:
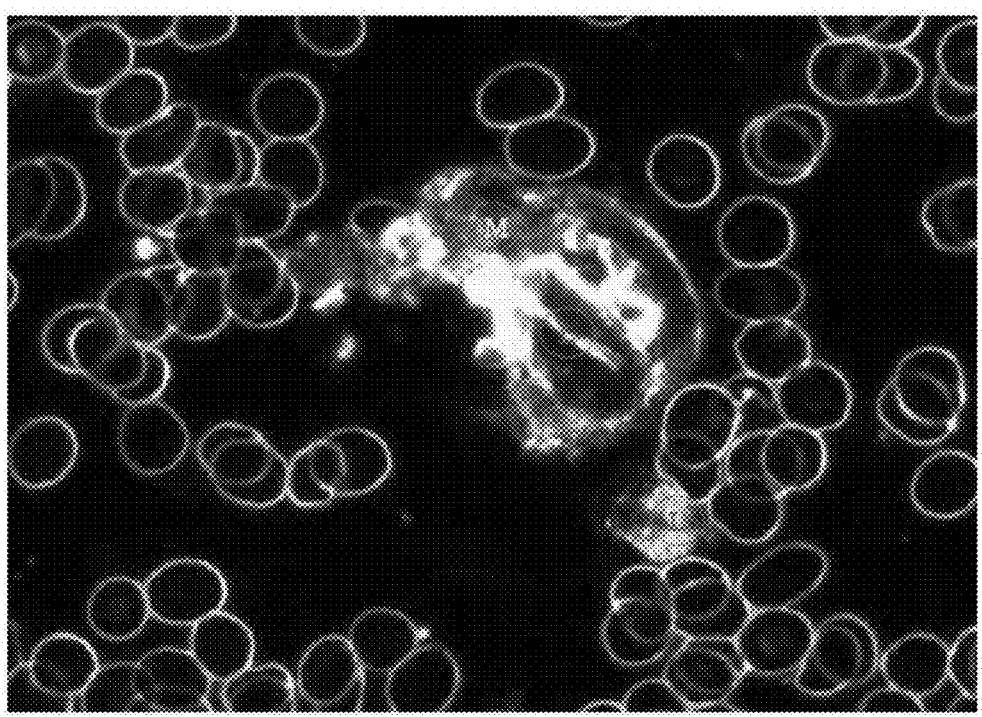
Figure 9C:
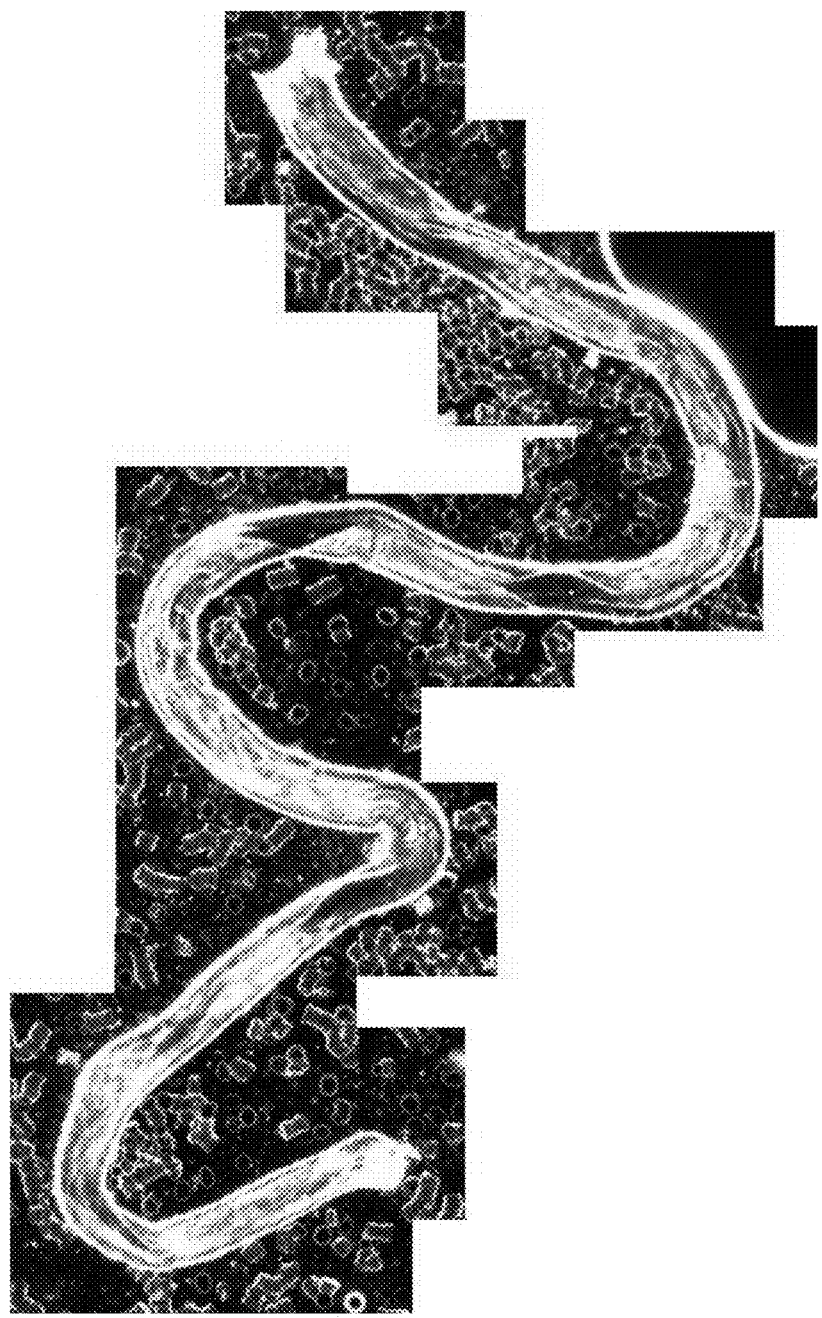
Figure 9D:
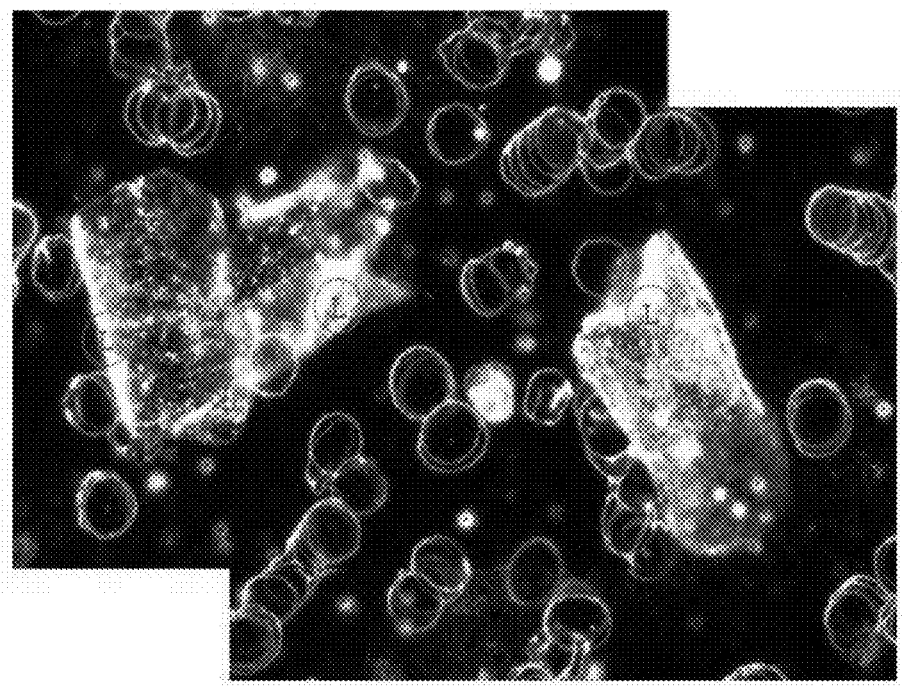
Figure 10:
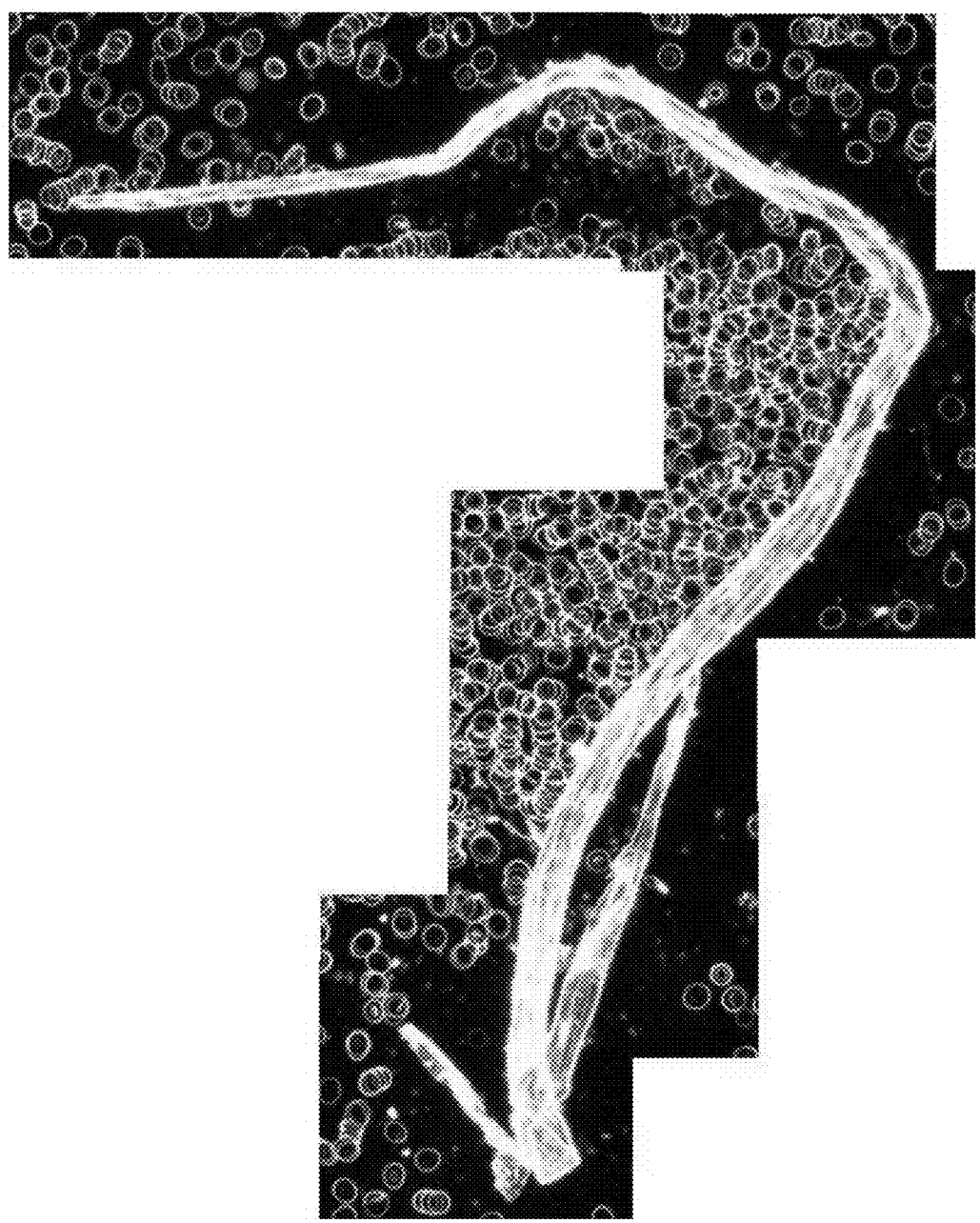
FIG. 10 is a photograph of luterial derived from a common bile duct cancer patient with a bone/pulmonary metastasis, photographed using the confocal laser scanning microscope.
Figure 11:
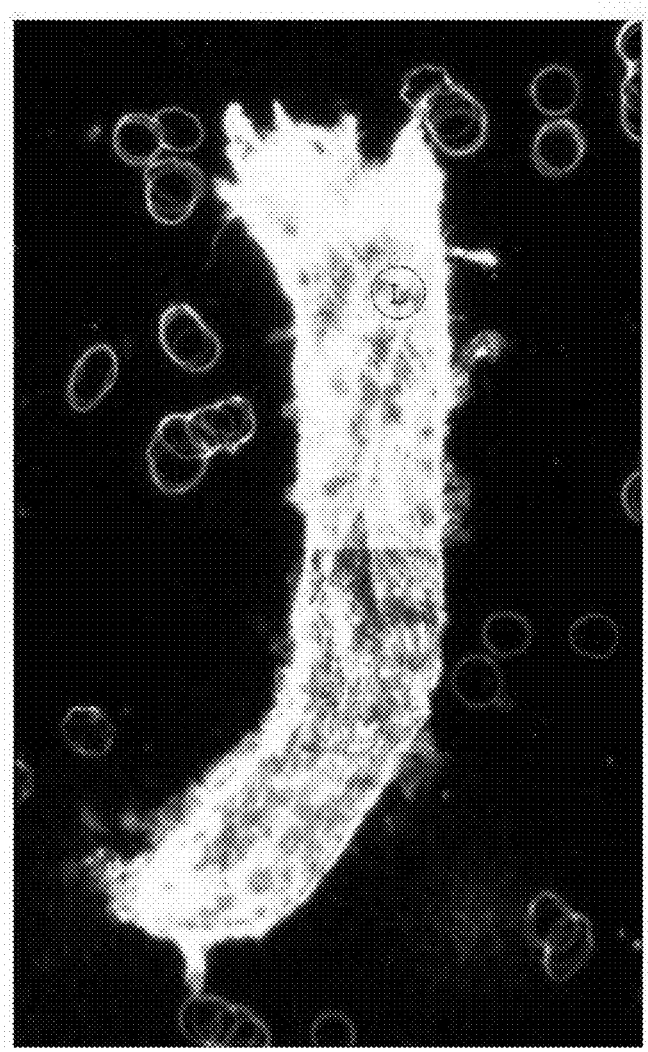
FIG. 11 is a photograph of luterial derived from a pleural mesothelioma patient, photographed using the dark field microscope.
Figure 12:
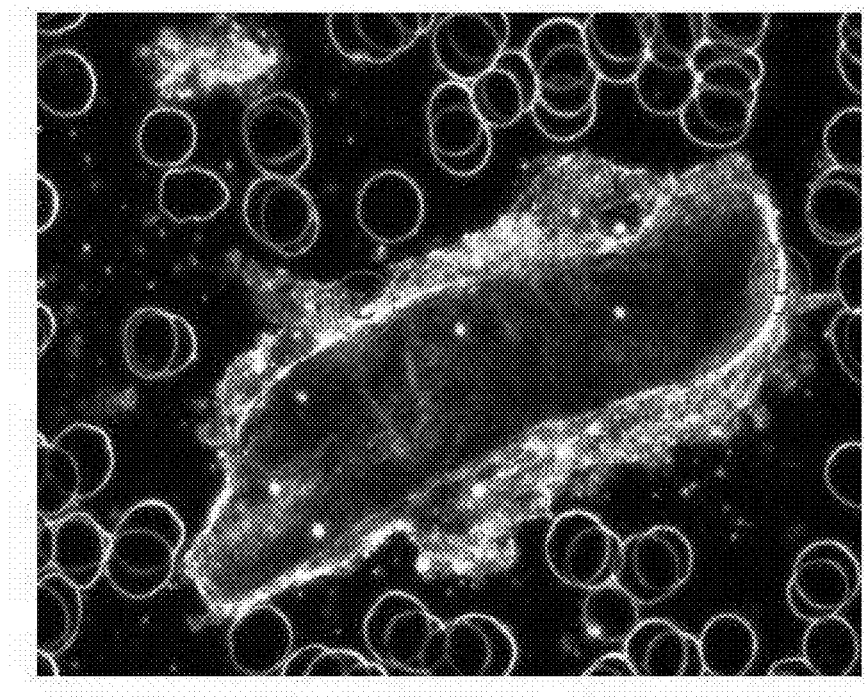
FIG. 12 is a photograph of luterial derived from a thyroid cancer patient (middle stage), photographed using the dark field microscope.
Figure 13A:
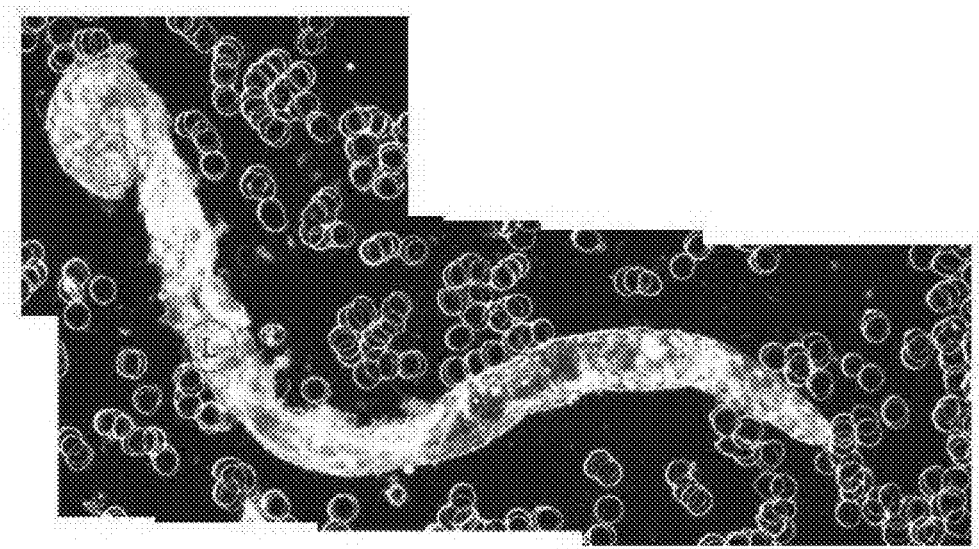
FIGS. 13A and 13B are photographs of luterial derived from ovarian cancer patients, photographed using the dark field microscope (FIGS. 13A/13B: middle stage).
Figure 13B:
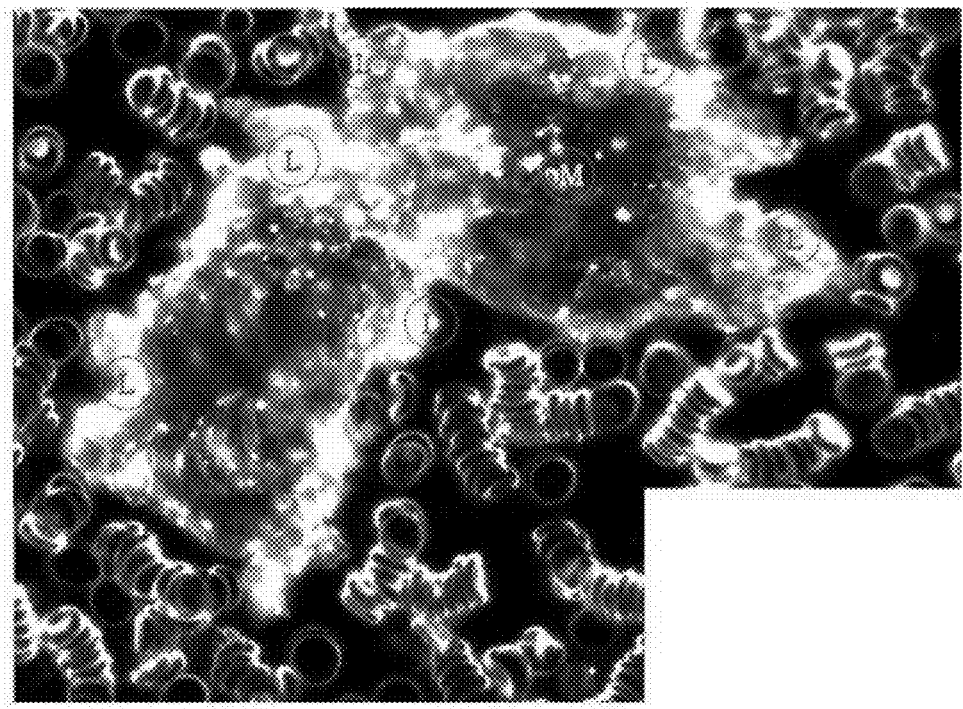
Figure 14:
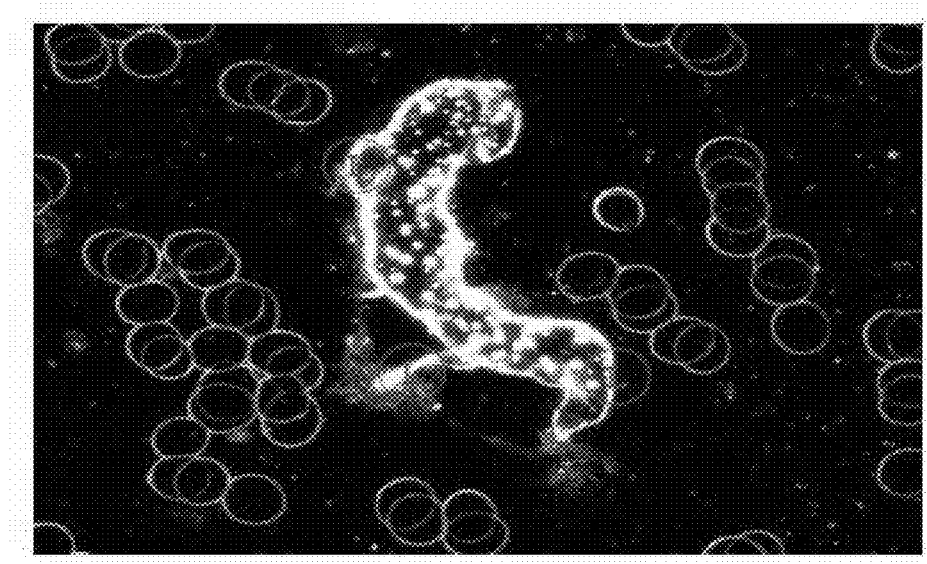
FIG. 14 is a photograph of luterial derived from a biliary tract cancer patient, photographed using the dark field microscope.
Figure 15:
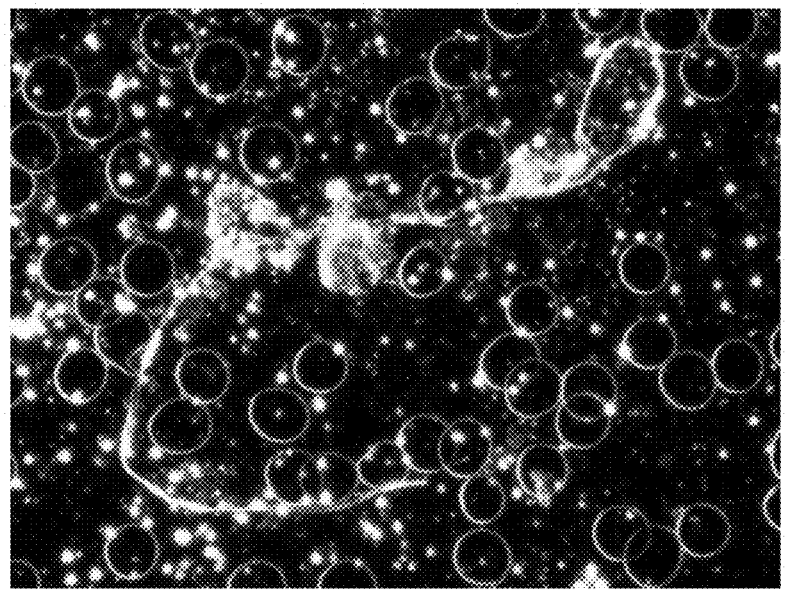
FIG. 15 is a photograph of luterial derived from a prostate cancer patient, photographed using the dark field microscope.
Figure 16A:
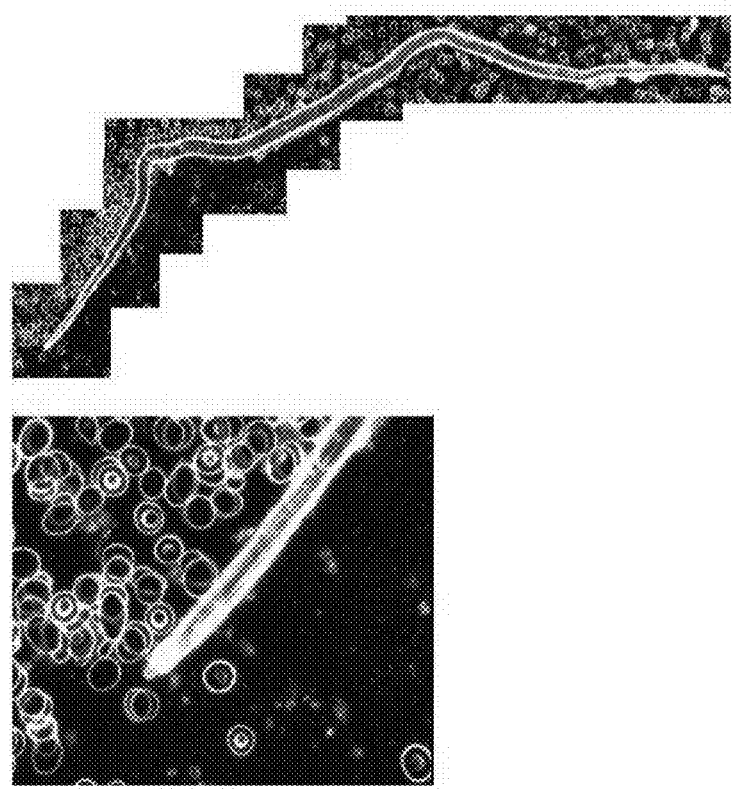
FIGS. 16A and 16B are photographs of luterial derived from acute lymphoblastic leukemia patients, photographed using the dark field microscope (FIG. 16A: middle stage.
Figure 16B:
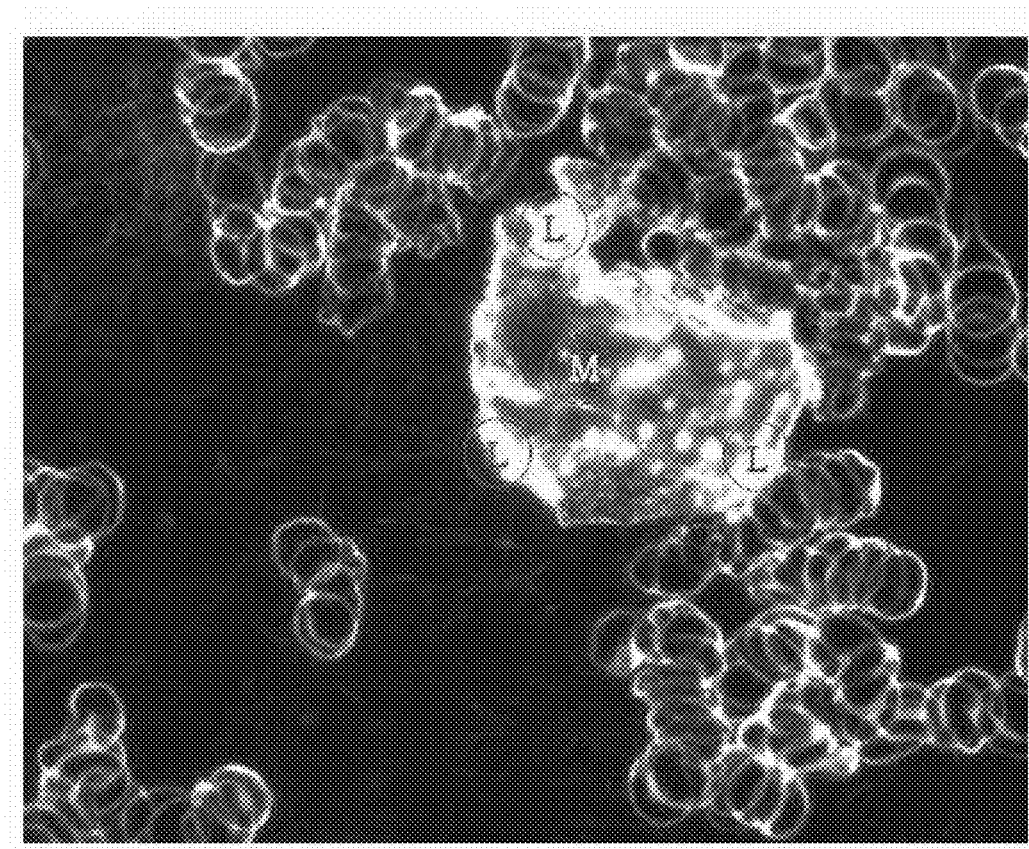
Figure 17A:
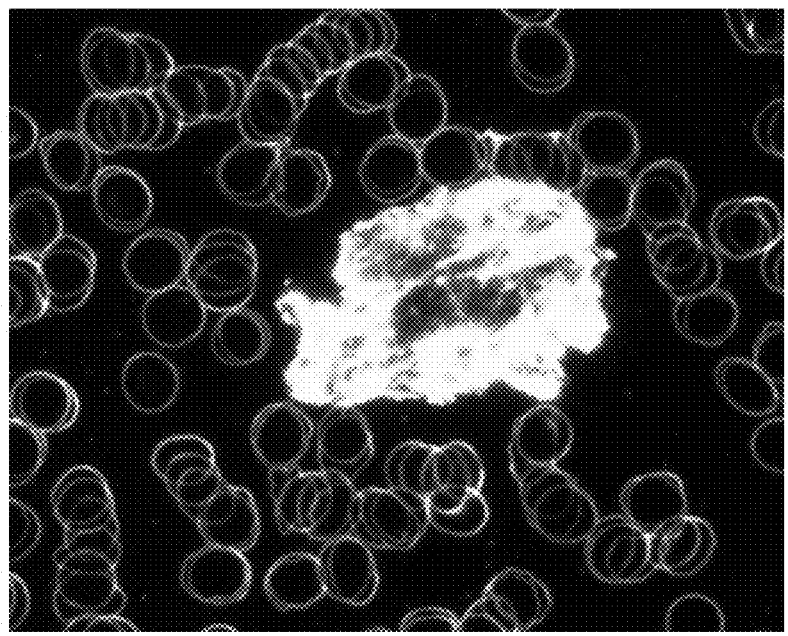
FIGS. 17A to 17C illustrate photographs of luterial derived from liver cancer patients, photographed using the dark field microscope (FIG. 17A: early stage, FIG. 17B/17C: middle stage, and FIG. 17D is a photograph of luterial derived from a liver cancer patient with pulmonary metastasis, photographed using the confocal laser scanning microscope).
Figure 17B:
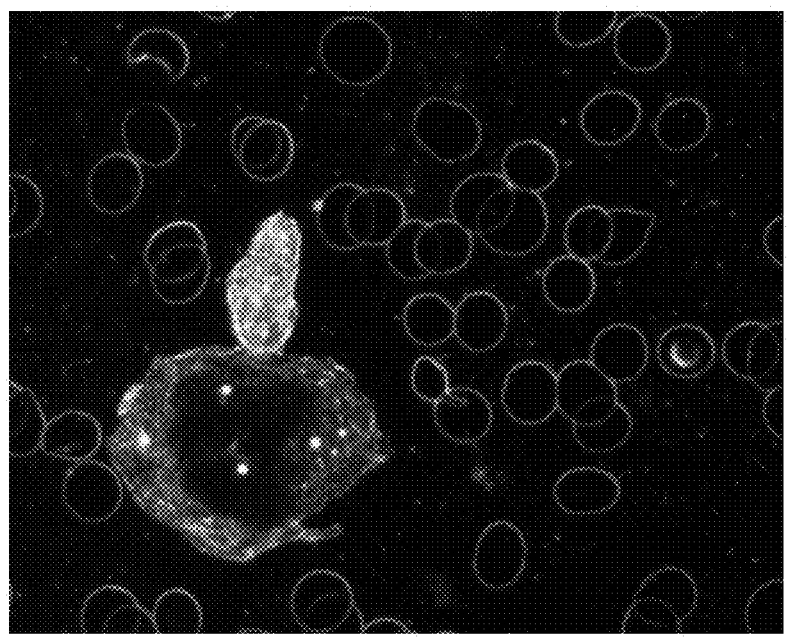
Figure 17C:
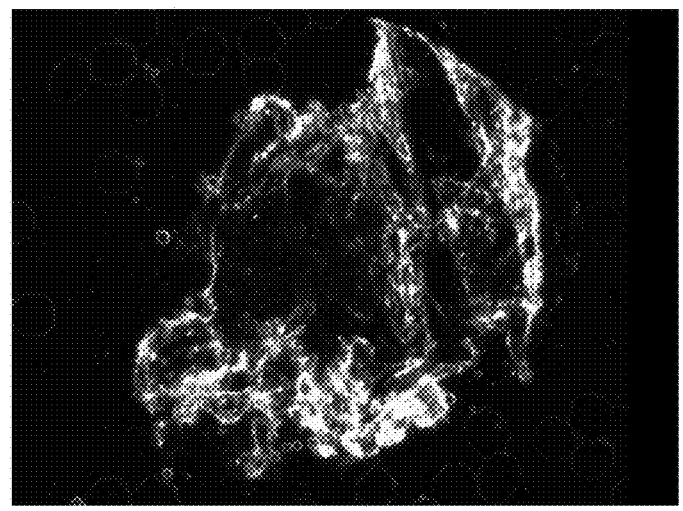
Figure 17D:
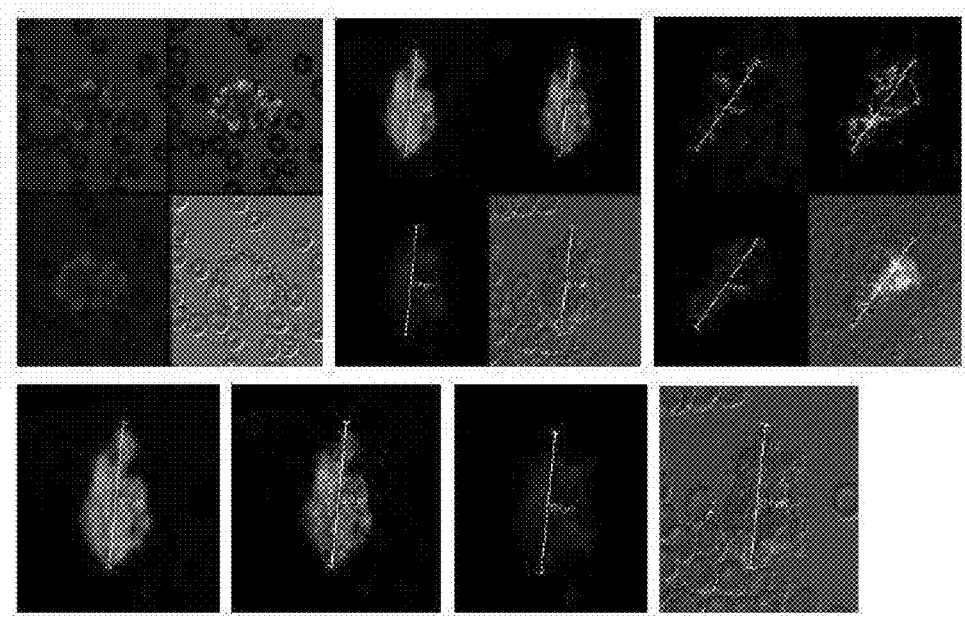
Figure 18:
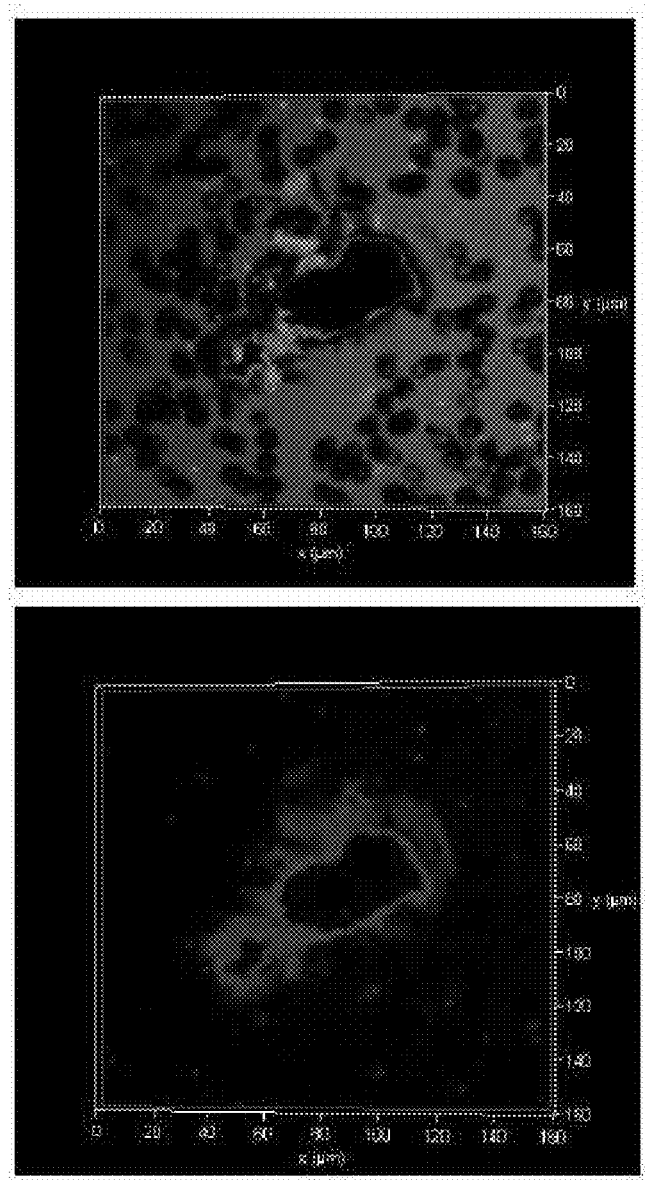
FIG. 18 illustrates a photograph of luterial derived from a patient with angiosarcoma of liver, photographed using the confocal laser scanning microscope.
Figure 19A:
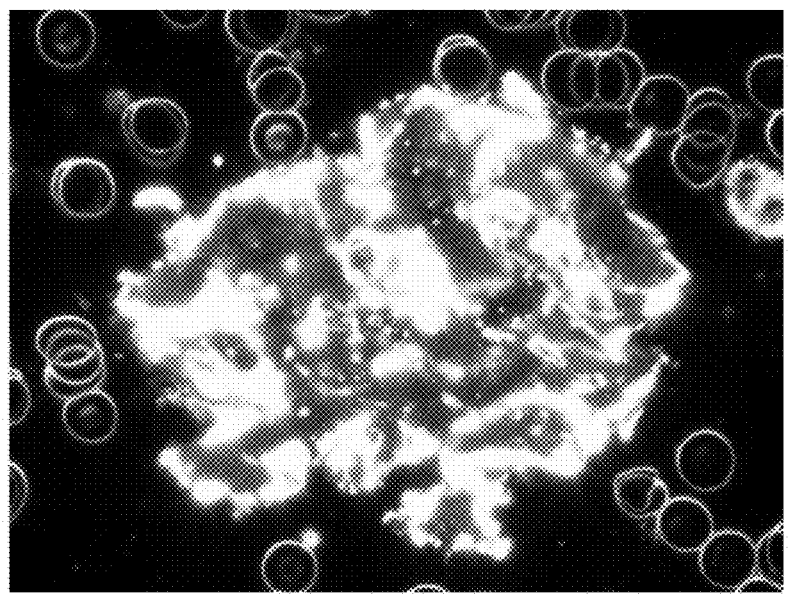
FIGS. 19A to 19C illustrate photographs of luterial derived from colon cancer patients, photographed using the dark field microscope.
Figure 19B:
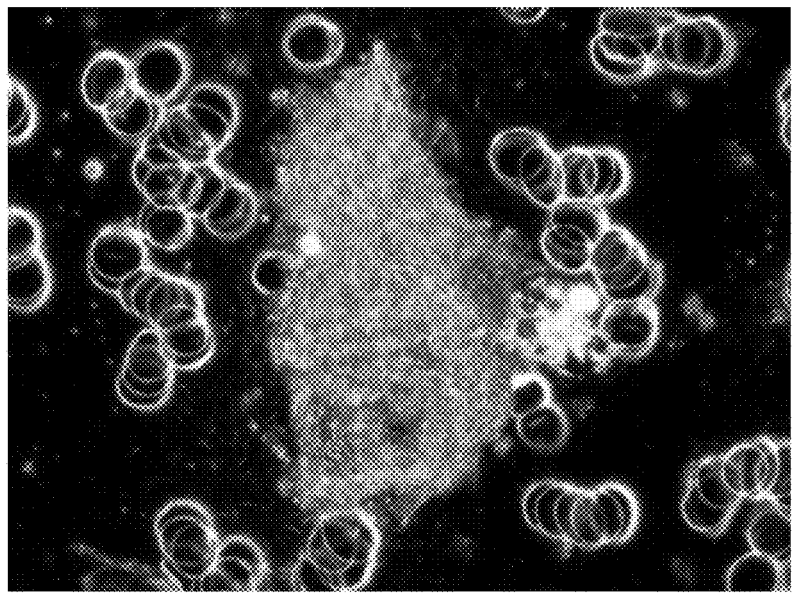
Figure 19C:
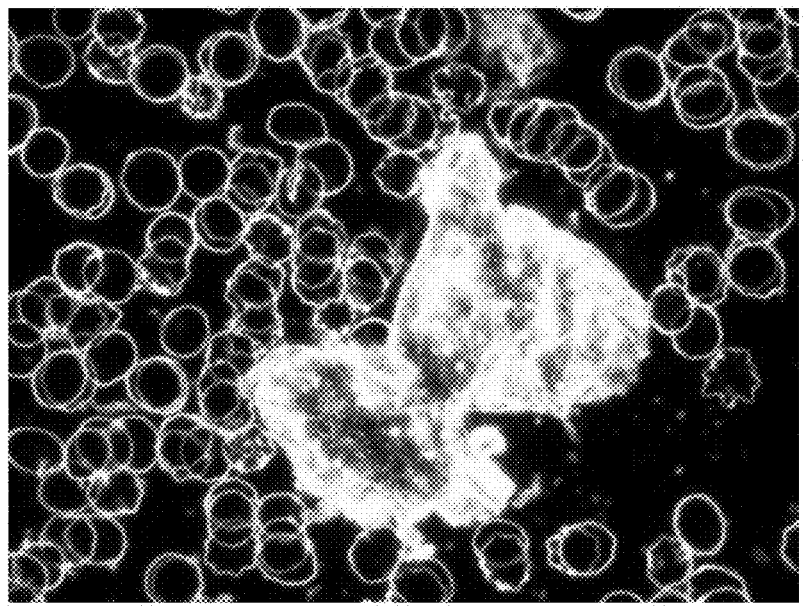
Figure 20:
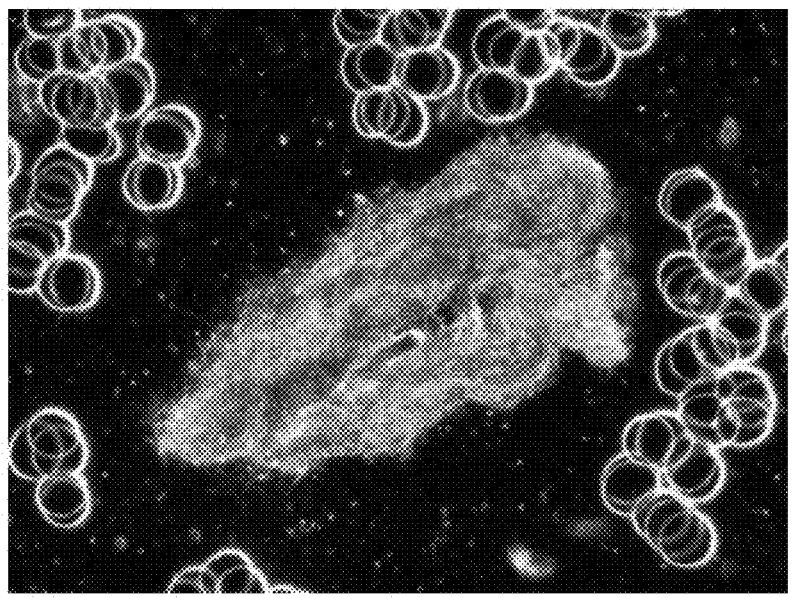
FIG. 20 is a photograph of luterial derived from a uterine cancer patient, photographed using the dark field microscope.
Figure 21:
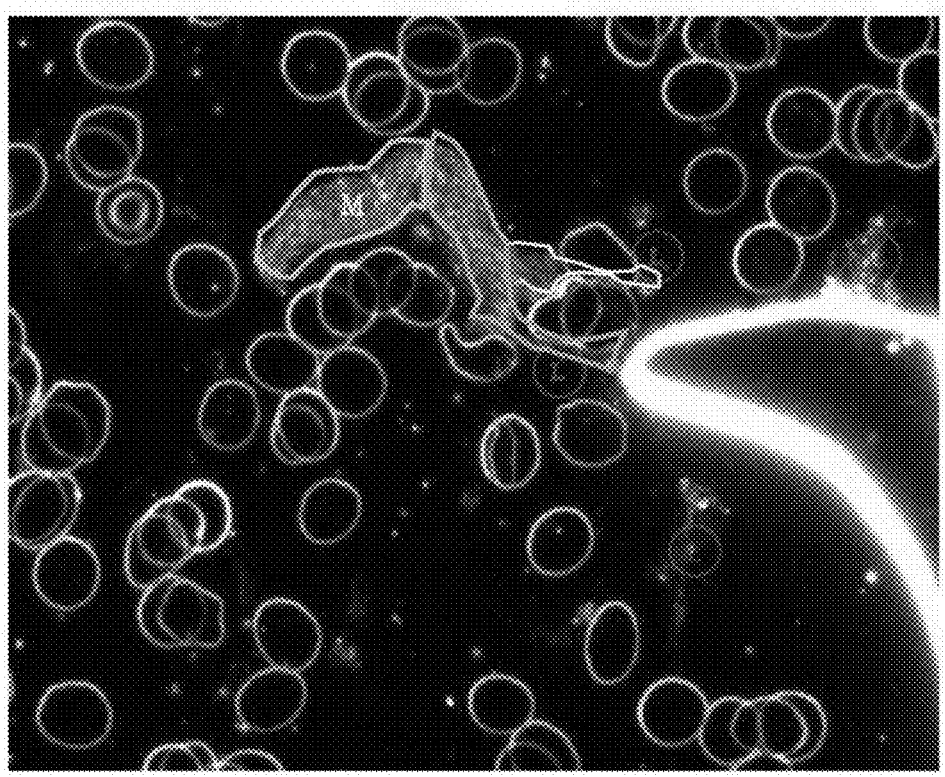
FIG. 21 is a photograph of luterial derived from an early-stage gastric cancer patient, photographed using the dark field microscope.
Figure 22A:
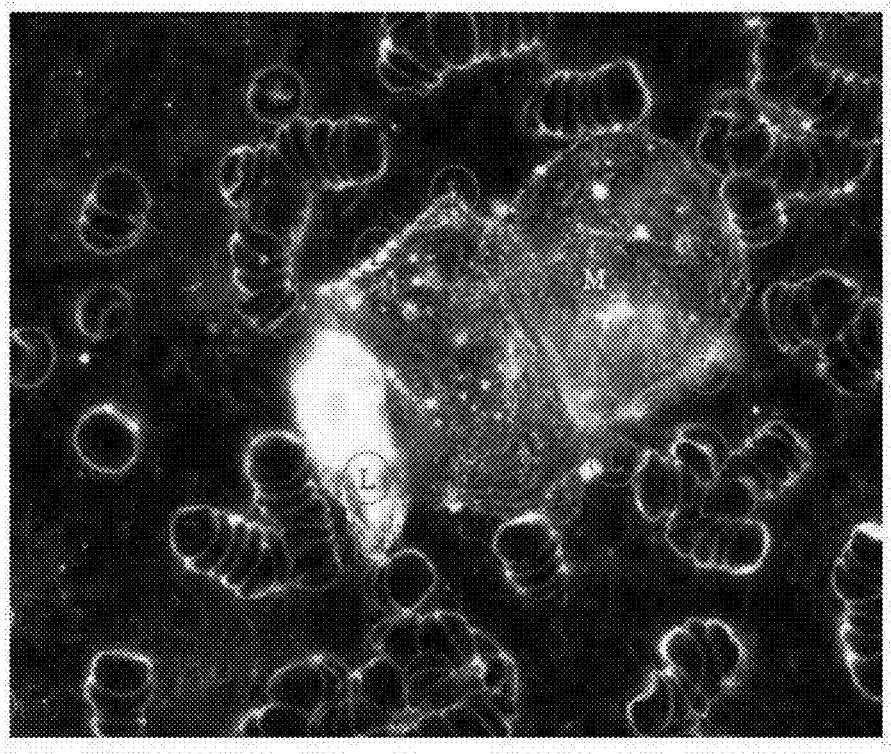
FIGS. 22A and 22B illustrate photographs of luterial derived from early-stage rectal cancer patients, photographed using the dark field microscope (FIG. 22A: mass-rod progressive shape.
Figure 22B:
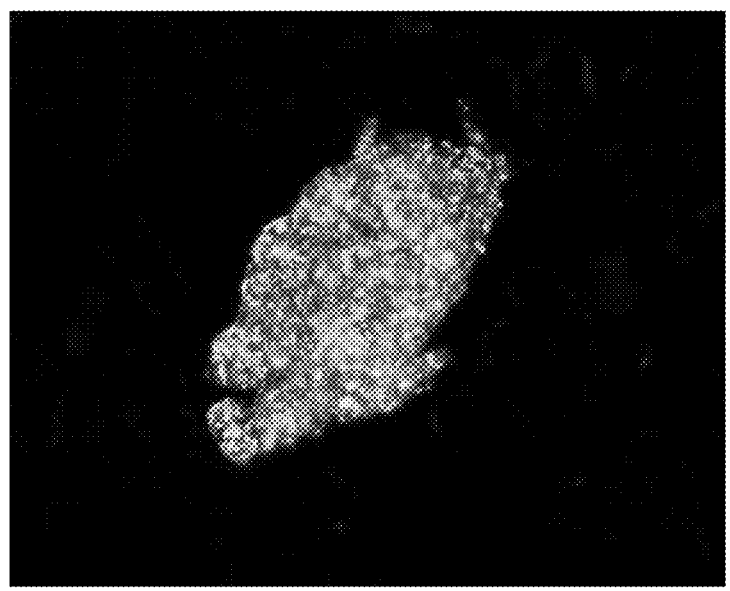
Figure 23A:
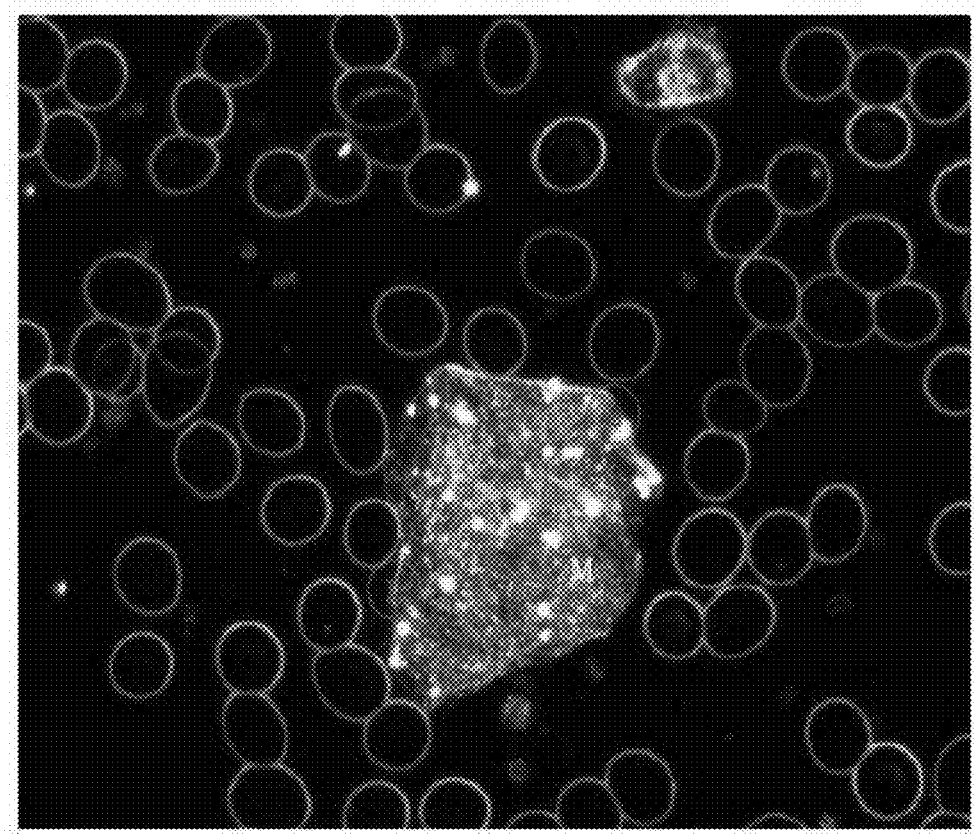
FIGS. 23A to 23C are photographs of luterial derived from acute myeloid leukemia patients, photographed using the dark field microscope (FIG. 23A: mass-rod progressive shape.
Figure 23B:
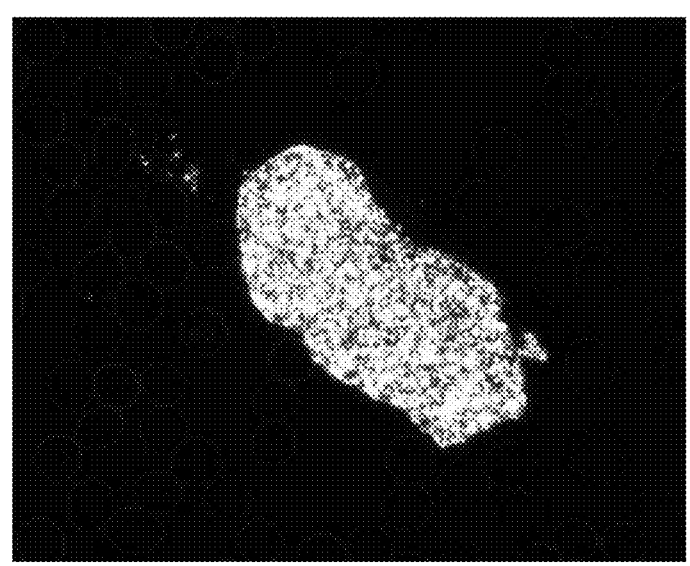
Figure 23C:
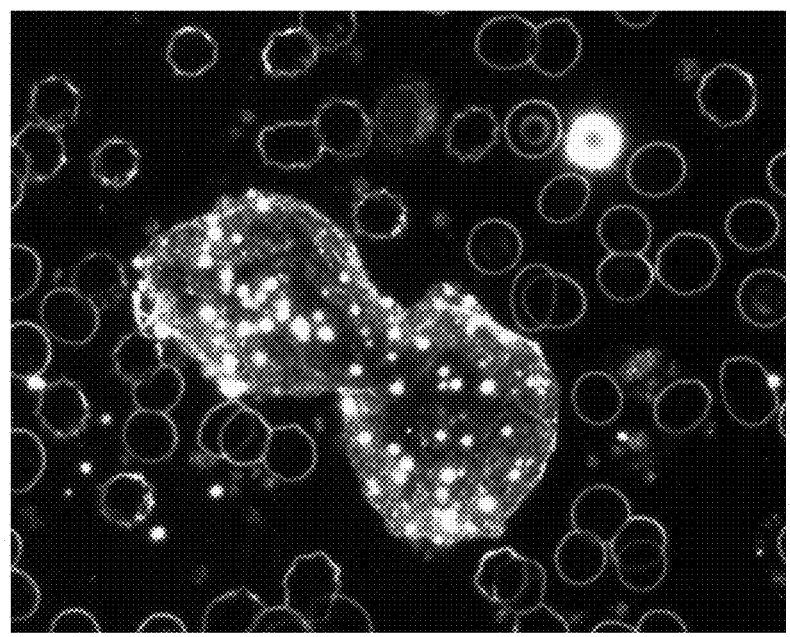
Figure 24:
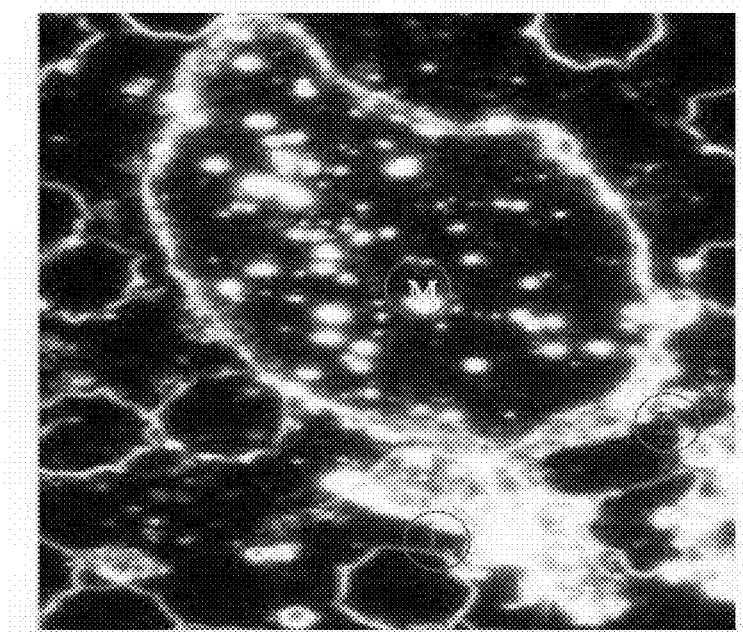
FIG. 24 is a photograph of luterial derived from an acute myeloid leukemia patient (mass-rod progressive shape), photographed using the dark field microscope.
Figure 25A:
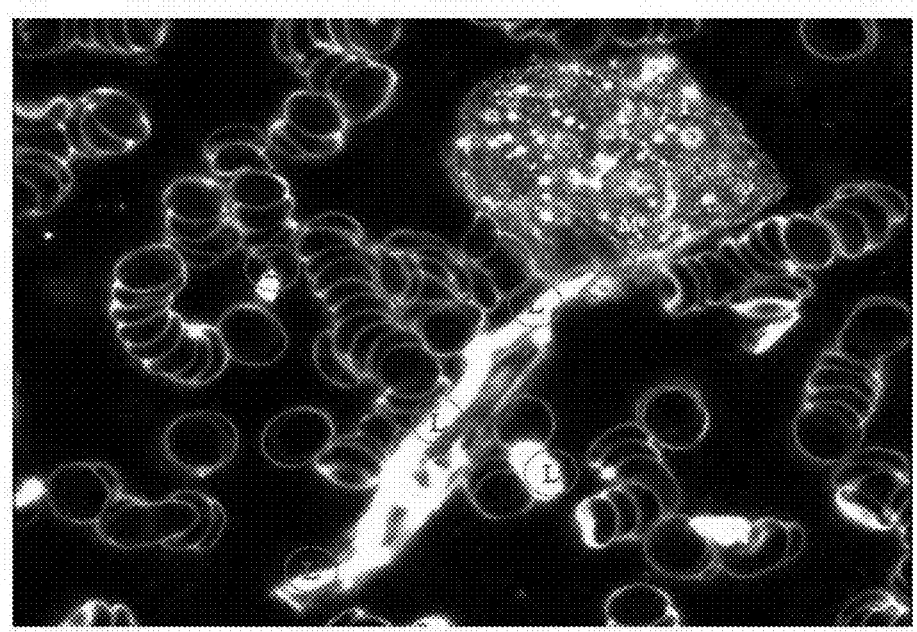
FIG. 25A illustrates luterial derived from a gastric cancer patient with hepatic metastasis.
Figure 25B:
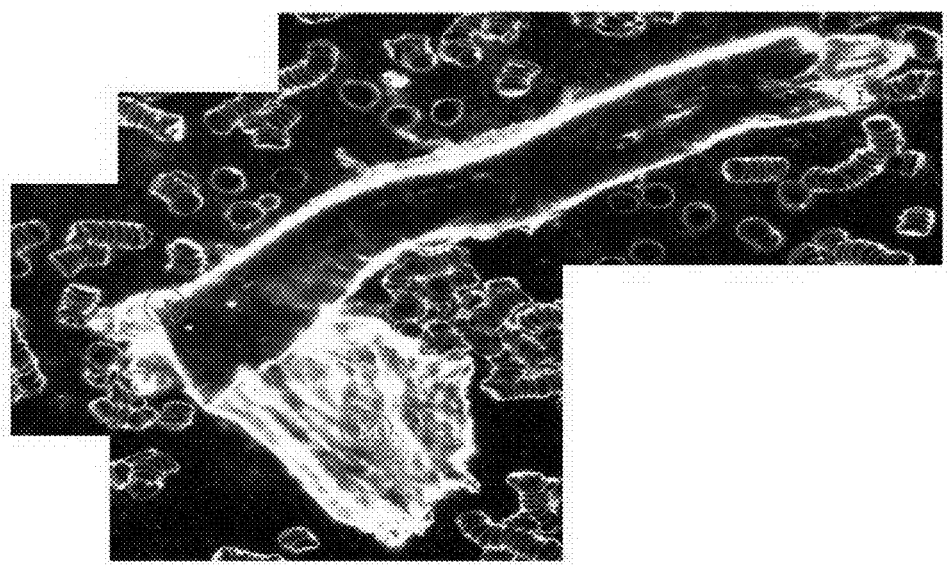
FIG. 25B illustrates luterial derived from a gastric cancer patient with peritoneal metastasis.
Figure 25C:
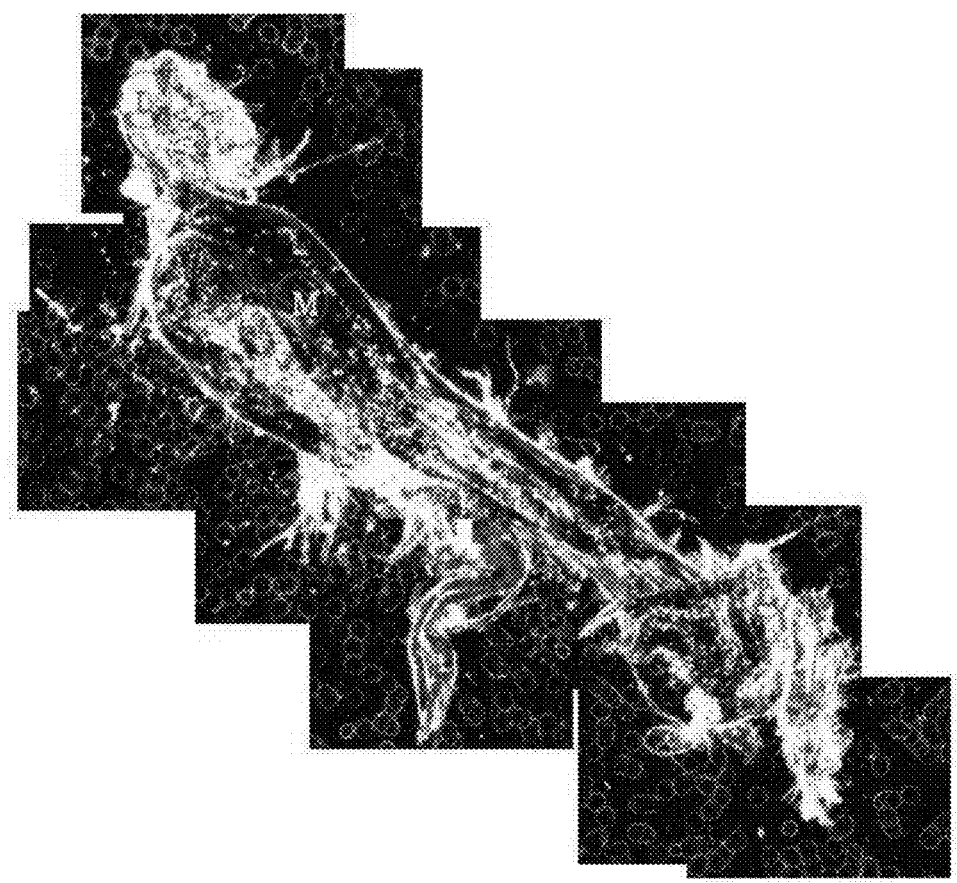
FIG. 25C illustrates luterial derived from a gastric cancer patient with peritoneal and hepatic metastasis.
Figure 26:
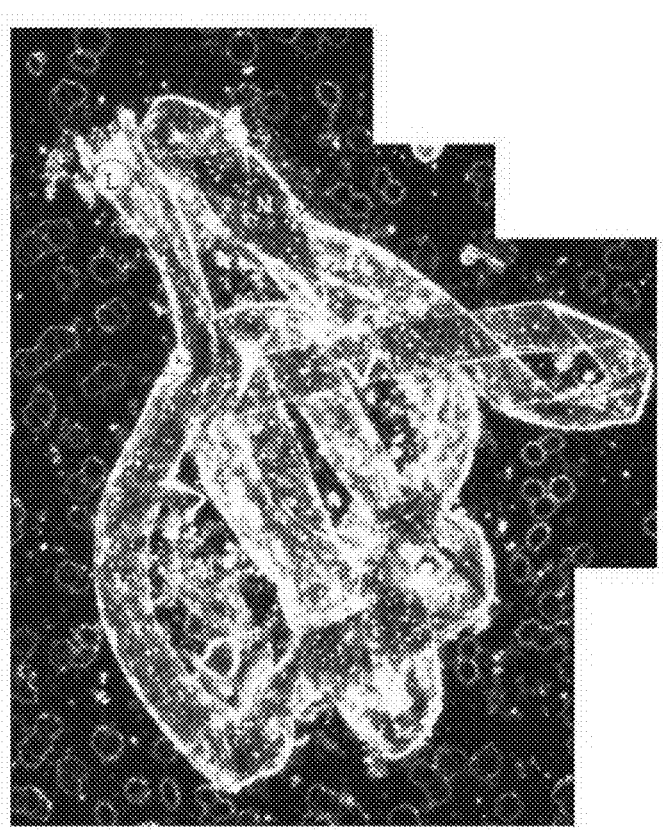
FIG. 26 illustrates luterial derived from a rectal cancer patient with bone metastasis and pulmonary metastasis.
Figure 27:
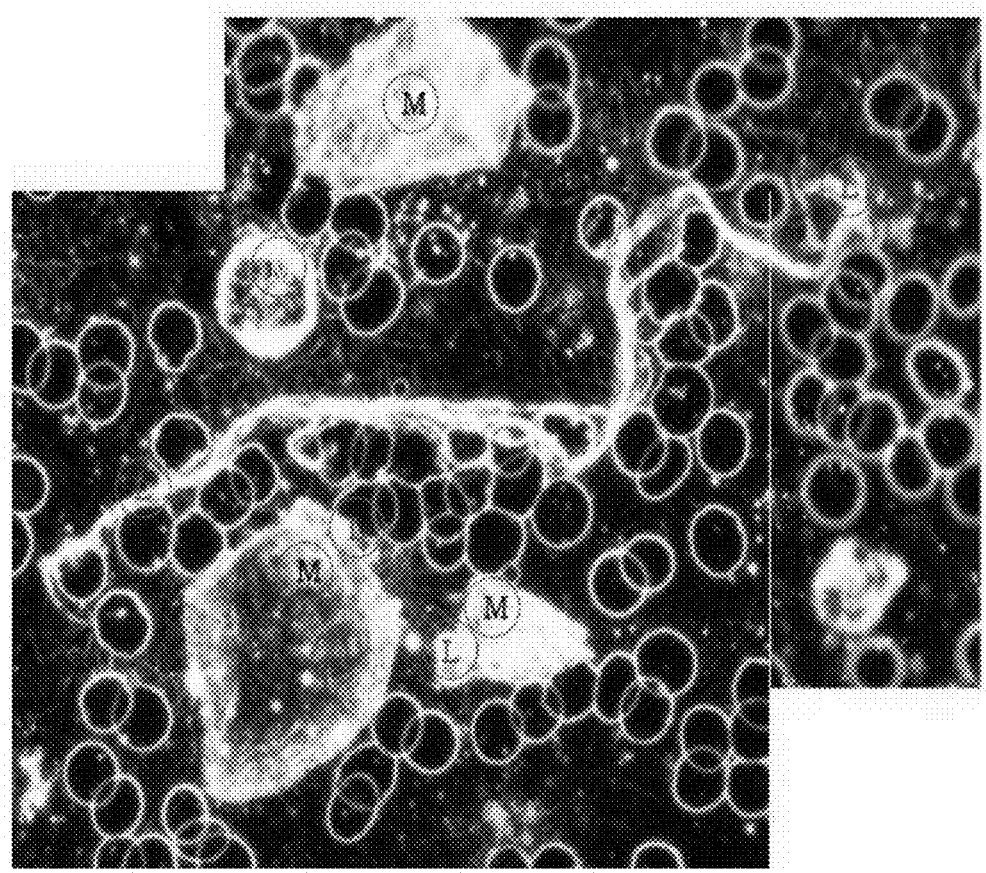
FIG. 27 illustrates luterial derived from a prostate cancer patient with bone metastasis.
Figure 28:
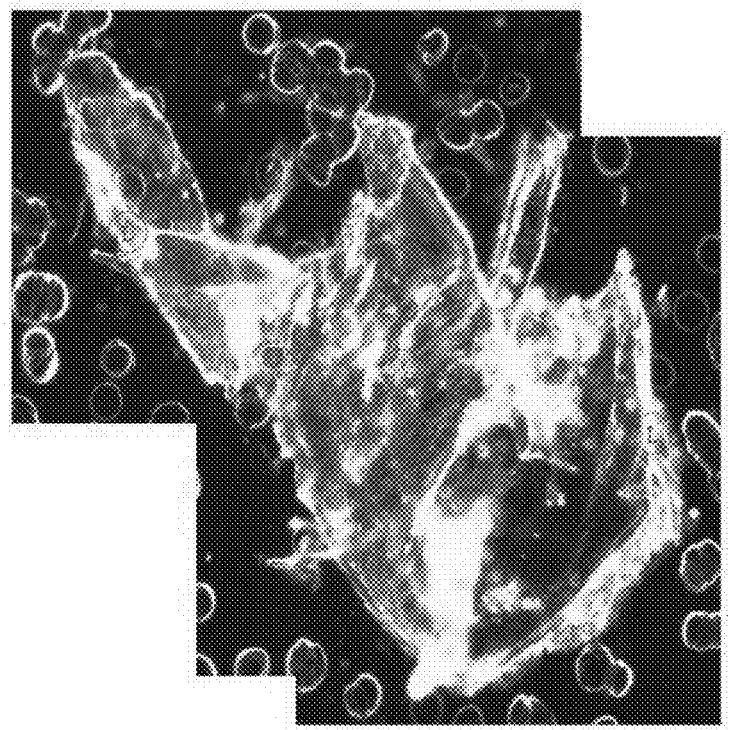
FIG. 28 illustrates luterial derived from a non-small cell lung cancer (NSCLC) patient with lymphogenous metastasis.
Figure 29:
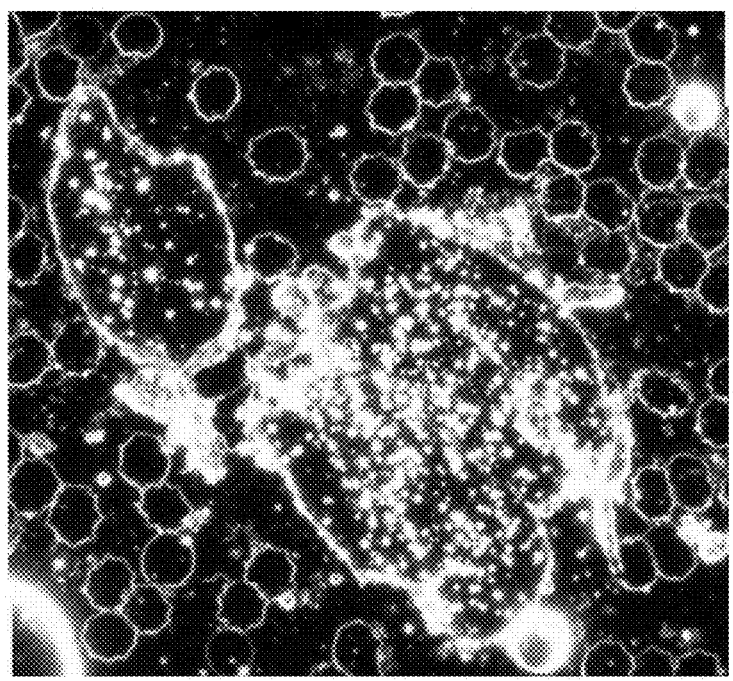
FIG. 29 is a photograph of luterial derived from a kidney cancer patient with bone metastasis, photographed using the dark field microscope.
Figure 30:
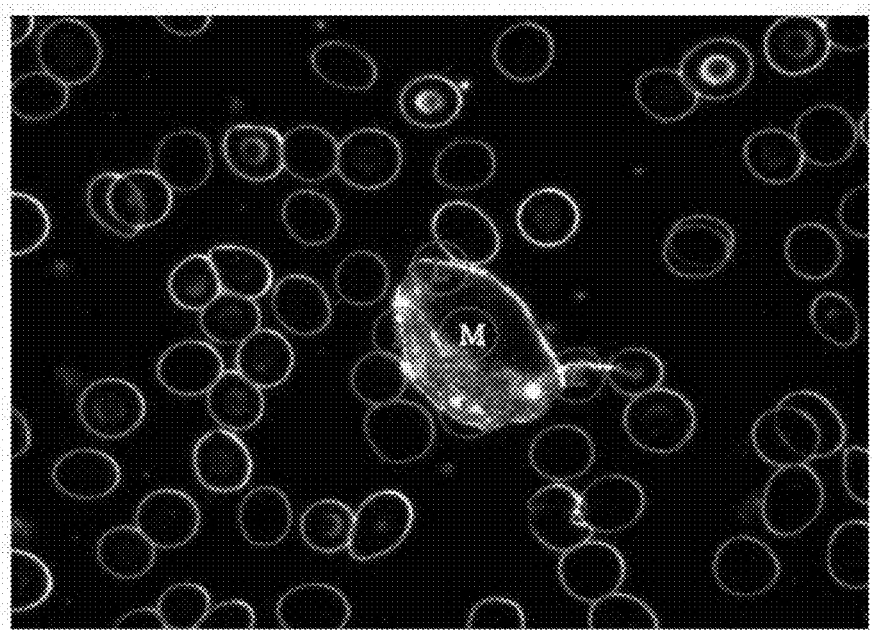
FIG. 30 is a photograph of luterial derived from an acute lymphoblastic leukemia patient, photographed using the dark field microscope.

| Type of cancer | Progress of cancer | Shape of luterial | FIGS. |
|---|---|---|---|
| lung cancer | early stage | L | FIG. 7a |
|  | middle stage | L | FIG. 7b~e |
| breast cancer | early stage | L | FIGS. 8a~b |
|  | middle stage | L | FIG. 8c |
|  | middle stage | L-M | FIG. 8d |
|  | lymphogenous, peritoneal and pericardial metastasis | L | FIG. 8e |
| pancreatic cancer | early stage | L | FIG. 9a |
|  | middle stage | L-M | FIG. 9b |
|  | middle stage | L | FIGS. 9c~d |
| Common Bile Duct Cancer | bone/pulmonary metastasis | L | FIG. 10 |
| Pleural Mesothelioma |  | L | FIG. 11 |
| thyroid cancer | early stage | L | FIG. 6 |
|  | middle stage | L | FIG. 12 |
| ovarian cancer |  | L-M | FIGS. 13a~b |
| biliary track cancer |  | L | FIG. 14 |
| prostate cancer |  | L | FIG. 15 |
| acute lymphoblastic leukemia |  | L | FIG. 16a |
|  |  | L-M | FIG. 16b |
| liver cancer | early stage | M | FIG. 17a |
|  | middle stage | M | FIGS. 17b~c |
|  | pulmonary metastasis | M | FIG. 17d |
| angiosarcoma of liver |  | M | FIG. 18 |
| colorectal cancer |  | M | FIGS. 19a~c |
| uterine cancer |  | M | FIG. 20 |
| gastric cancer (stomach cancer) |  | M-L | FIG. 21 |
| rectal cancer | middle stage | M-L | FIG. 22a |
|  | middle stage | M | FIG. 22b |
| acute myeloid leukemia | middle stage | M-L | FIG. 23a |
|  |  | M | FIGS. 23b~c |
| acute myeloid leukemia | middle stage | M-L | FIG. 24 |
| gastric cancer (stomach cancer) | liver metastasis | complex | FIG. 25a |
| gastric cancer (stomach cancer) | peritoneal metastasis | complex | FIG. 25b |
| gastric cancer (stomach cancer) | peritoneal and liver metastasis | complex | FIG. 25c |
| rectal cancer | bone/pulmonary metastasis | complex | FIG. 26 |
| prostate cancer | bone metastasis | complex | FIG. 27 |
| non-small cell lung cancer (NSCLC) | lymphogenous metastasis | complex | FIG. 28 |
| uterine cancer | bone metastasis | complex | FIG. 29 |
| acute lymphoblastic leukemia |  | complex | FIG. 30 |

As a result, in the method for diagnosis and prognosis prediction of diseases according to the present invention, when the shape of the observed or photographed luterial is the rod shape, a patient may be determined to be in a lung cancer, breast cancer, pancreatic cancer, common bile duct cancer, pleural mesothelioma, thyroid cancer, ovarian cancer, biliary track cancer, prostate cancer, or lymphoblastic blood cancer development state.

Further, in the method for diagnosis and prognosis prediction of diseases according to the present invention, when the shape of the observed or photographed luterial is the mass shape, a patient may be determined to be in a liver cancer, angiosarcoma of liver, colorectal cancer, uterine cancer, gastric cancer (stomach cancer), rectal cancer, kidney cancer, or myeloid blood cancer development state.

Furthermore, in the method for diagnosis and prognosis prediction of diseases according to the present invention, when the shape of the luterial is the complex shape, a patient may be determined to be in a severe blood cancer or metastasis suspected state, and when the flagellum-shaped luterial was detected, a patient may be determined to be in an end-stage cancer suspected state.

Example 8: Diagnosis and Prognosis Prediction of Diseases Depending on Nano-Tracking Speed of Luterial Luterial was obtained from bloods of stage-1, stage-2, stage-3, and stage-4 cancer patients (Each stage: 15 patients) by the same method as in Example 1. The luterial was put into the buffer solution and stained with Janus Green B, and then, observed using an optical microscope.

Figure 31:
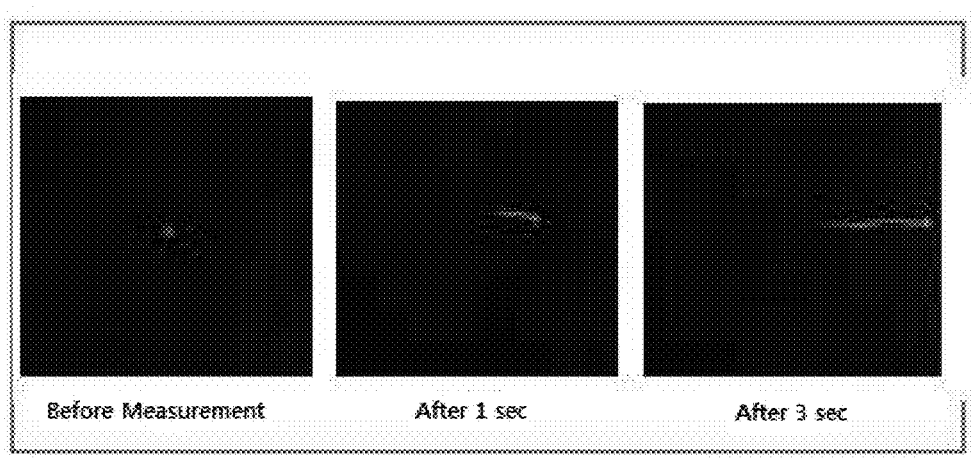
FIG. 31 is a photograph obtained by measuring a movement speed (nano-tracking speed) of luterial using a nano tracker.

As a basis of motility, a nano-tracking speed of luterial was measured using luterial having a size of 200 nm and nano-tracking (3i Corp, US). In detail, after observing the luterial using a bright field microscope, at the time of setting tracking at the center of the luterial, and operating the nano-tracking, a real-time movement track was shown together with movement of the luterial, thereby calculating a speed per second (FIG. 31).

TABLE 4

|  | Nano-Tracking Speed |
|---|---|
| Normal | 12 μm/sec or more |
| Cancer stage 1 | 8.0~11 μm/sec |
| Cancer stage 2 | 5.0 μm/sec or so(2.5~8.0 μm/sec) |
| Cancer stage 3 | 0.5~2.5 μm/sec |
| Cancer stage 4 | No motility (0~0.5 μm/sec) |

The nano-tracking speed of the luterial derived from the cancer patient according to the present Example indicates motility of the luterial. In a normal person, the nano-tracking speed was 12 μm/sec or more, but it was observed that as a stage of cancer increased from stage 1 corresponding to an early stage to stage 4 corresponding to an end stage, the motility decreased, such that in stage-4 cancer, there was almost no motility. Therefore, in the method for diagnosis and prognosis prediction of diseases according to the present invention, in a case in which the nano-tracking speed of the observed or photographed luterial is 8.0 to 11 μm/sec, a patient may be determined to be a stage 1 cancer patient, in a case in which the nano-tracking speed of the luterial is 2.5 to 8.0 μm/sec, a patient may be determined to be a stage 2 cancer patient, in a case in which the nano-tracking speed of the luterial is 0.5 to 2.5 μm/sec, a patient may be determined to be a stage 3 cancer patient, and in a case in which the nano-tracking speed of the luterial is 0 to 0.5 μm/sec, a patient may be determined to be a stage 4 cancer patient.

Example 9: Diagnosis and Prognosis Prediction of Disease Depending on Shape of Luterial Using Electron Microscope In a case of observing the luterial using an electron microscope, a single shape, a fused shape, a multi-fused shape, and a fused shape in which a membrane is ruptured may be shown, and it is possible to diagnose a disease and to predict prognosis of the disease based on the observed shape.

The single shape is a shape observed in a single luterial, the fused shape is a shape observed when two to four luterial clusters are fused, a multi-fused shape is a shape observed when the fused luterial clusters are fused over and over again, and the fused shape in which the membrane is ruptured is a shape observed when a membrane of the fused luterial is ruptured, and internal materials thereof are discharged.

Luterial was obtained from bloods of various subjects (30 persons) from normal persons to end-stage cancer patients by the same method as in Example 1. The obtained luterial was fixed onto a slide glass, and the shape of the luterial was observed or photographed using the electron microscope.

As a result, in the normal person, luterial having the single shape was observed. In patients having diseases except for cancer, luterial having the fused shape was observed, and thus, it may be judged that the patient is suspected to have a disease, if luterial has the fused shape.

In a plurality of patients in which luterial having the multi-fused shape was observed, a tumor was found. Therefore, it may be judged that the luterial having the multi-fused shape is a marker of a tumor suspected state.

Figure 32A:
FIGS. 32A to 32C are photographs illustrating shapes of luterial having a fused shape in which a membrane is ruptured, sequentially photographed using an electron microscope.
Figure 32B:
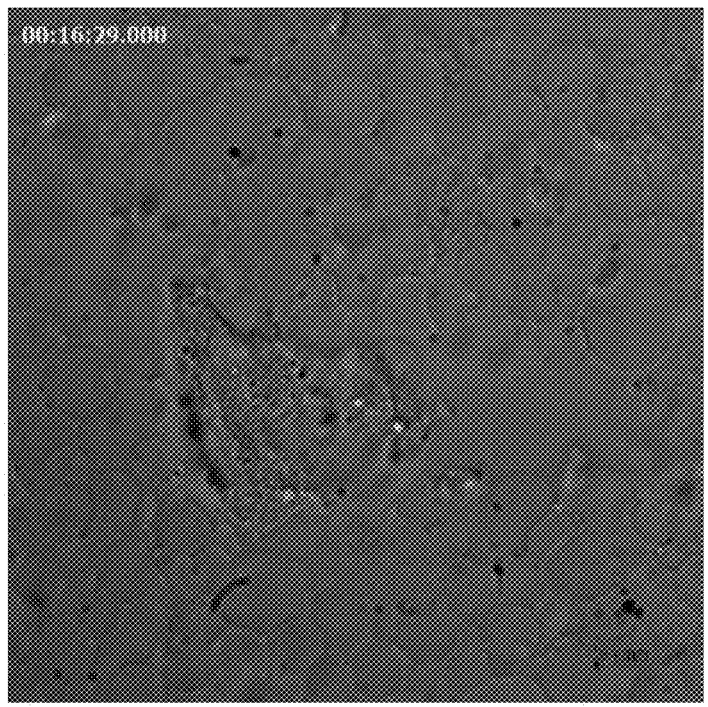
Figure 32C:
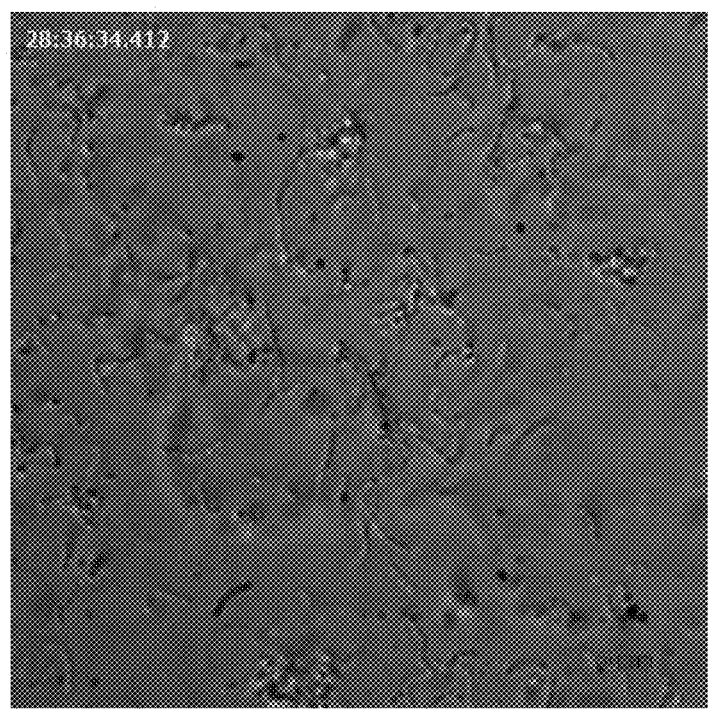

FIGS. 32A to 32C are photographs illustrating shapes of luterial having a fused shape in which a membrane is ruptured, sequentially photographed using an electron microscope. The luterial cluster forming a membrane (FIG. 32A) was gradually proliferated (FIG. 32B), such that finally, the membrane was ruptured and deformed particles therein were discharged (FIG. 32C). In a plurality of patients in which the luterial had the fused shape in which the membrane was ruptured, severe cancer was found. Therefore, it may be judged that the luterial having the fused shape in which the membrane is ruptured is a marker of a severe cancer suspected state.

Therefore, in the method for diagnosis and prognosis prediction of diseases according to the present invention, at the time of comparing the shape of the luterial which exists in the blood and of which the double membrane structure and the cristae structure were confirmed on the electron microscope, a case in which, the shape of the luterial coincides with 80 to 100% of the single normal shape may be determined to be normal, a case in which the shape coincides with 80 to 100% of the fused shape may be determined to be in a disease suspected state, a case in which the shape coincides with 80 to 100% of the multi-fused shape may be determined to be in a tumor suspected state, and a case in which the shape coincides with 80 to 100% of the fused shape in which the membrane is ruptured may be determined to be in a severe tumor suspected state.

Therefore, in the method for diagnosis and prognosis prediction of diseases according to the present invention, the luterial is used as the marker for diagnosis and prognosis prediction of the diseases, such that the luterial may be effectively used to diagnose, particularly, a cancer patient, determine the presence or absence of an effect of a treatment method, compare effects before and after treatment, and judge whether or not a patient subjected to treatment may survive for a long period of time.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

INDUSTRIAL APPLICABILITY

According to the present invention, luterial, which is a micromaterial existing in blood fluid already excreted from a patient, is used as a marker for diagnosis and prognosis prediction of diseases, such that the luterial may be effectively used to diagnose, particularly, a cancer patient, determine the presence or absence of an effect of an operation method and treatment method, compare effects before and after treatment, and judge whether or not a patient subjected to treatment may survive for a long period of time. Particularly, regardless of the kind of cancer, even though a size of cancer tissue is 5 mm or less, it is possible to judge a present state of cancer, a recurrence probability of cancer, and a long-term survival probability of a patient.

Further, since diseases may be automatically diagnosed and prognosis of the diseases may be predicted only by microscopic observation without using a separate gene analysis and expensive equipment, biopsy or expensive image diagnosis is unnecessary, such that the method according to the present invention has economical advantages.

The invention claimed is:
1. A method of treating a cancer patient, said method comprising:
   (a) imaging luterial from a sample of a body fluid of the patient, by microscopy, to present luterial shape(s), wherein the patient has a cancer selected from the group consisting of lung cancer, breast cancer, pancreatic cancer, common bile duct cancer, pleural mesothelioma thyroid cancer, ovarian cancer, biliary track cancer, prostate cancer, acute lymphoblastic leukemia, liver cancer, angiosarcoma of liver, colorectal cancer, uterine cancer, gastric cancer, rectal cancer, acute myeloid leukemia, rectal cancer, and non-small cell lung cancer;
   (b) based on the luterial shape(s) in the luterial imaged by microscopy from the sample of the body fluid of the patient, diagnosing a progressionary stage of said cancer; and
   (c) administering to the cancer patient a cancer treatment based on the progressionary stage of said cancer that is diagnosed in step (b).
2. The method of claim 1, wherein the luterial shape(s) on which said diagnosing is based comprises one or more shapes selected from the group consisting of rod shapes, rod-mass shapes, mass-rod shapes, mass shapes, and complex shapes.
3. The method of claim 1, wherein said imaging, by microscopy, is conducted with an optical microscope, confocal laser scanning microscope, or electron microscope.
4. The method of claim 1, wherein said imaging, by microscopy, is conducted with a dark field microscope.
5. The method of claim 1, wherein said imaging, by microscopy, comprises microscopic observation of the luterial from the sample of the body fluid of the patient.
6. The method of claim 1, wherein said imaging, by microscopy, comprises photographing the luterial from the sample of the body fluid of the patient.
7. The method of claim 1, wherein the body fluid of the patient is blood, saliva, lymph, semen, vaginally mucus, breast milk, umbilical cord blood, brain cells, spinal cord, or bone marrow.
8. The method of claim 1, wherein the body fluid of the patient is blood.
9. The method of claim 1, wherein said diagnosing in step (b) is also based on number of the luterial from the sample of the body fluid of the patient.
10. The method of claim 1, wherein said diagnosing in step (b) is also based on size of the luterial from the sample of the body fluid of the patient.

11. The method of claim 1, wherein said diagnosing in step (b) is also based on membrane formation of the luterial from the sample of the body fluid of the patient.

12. The method of claim 1, wherein said diagnosing in step (b) is also based on nano-tracking speed of the luterial from the sample of the body fluid of the patient.

13. The method of claim 1, wherein said diagnosing in step (b) is also based on two or more selected from the group consisting of:
- number of the luterial from the sample of the body fluid of the patient;
- size of the luterial from the sample of the body fluid of the patient;
- membrane formation of the luterial from the sample of the body fluid of the patient; and
- nano-tracking speed of the luterial from the sample of the body fluid of the patient.

14. The method of claim 1, wherein the luterial from the sample of the body fluid of the patient prior to said imaging is stained with a fluorescent staining agent, and said imaging, by microscopy, is conducted with a fluorescent microscope.

* * * * *

UNITED STATES PATENT AND TRADEMARK OFFICE
CERTIFICATE OF CORRECTION

PATENT NO.       : 10,338,061 B2
APPLICATION NO.  : 14/904507
DATED            : July 2, 2019
INVENTOR(S)      : Young Ah Kwon Page 1 of 1

It is certified that error appears in the above-identified patent and that said Letters Patent is hereby corrected as shown below:

On the Title Page

Item [56], insert the following references, after "2009/0311664 A1 12/2009 Fong, et al.":
--20160324896 A1 11/2016 Choi, et al.
20160334389 A1 11/2016 Choi, et al.--

Signed and Sealed this
Twentieth Day of August, 2019

Andrei Iancu
*Director of the United States Patent and Trademark Office*